US011387087B2

(12) United States Patent
Lefew et al.

(10) Patent No.: US 11,387,087 B2
(45) Date of Patent: Jul. 12, 2022

(54) METHOD FOR ANALYZING SMALL MOLECULE COMPONENTS OF A COMPLEX MIXTURE, AND ASSOCIATED APPARATUS AND COMPUTER PROGRAM PRODUCT

(71) Applicant: Metabolon, Inc., Morrisville, NC (US)

(72) Inventors: William Lefew, Cary, NC (US); David V. Foster, Durham, NC (US); Rex A. Dwyer, Raleigh, NC (US); Shelby S. Matlock, Durham, NC (US); Casson Stallings, Chapel Hill, NC (US); Michael Humphrey, Durham, NC (US); Michael Heiser, Cary, NC (US)

(73) Assignee: Metabolon, Inc., Morrisville, NC (US)

( * ) Notice: Subject to any disclaimer, the term of this patent is extended or adjusted under 35 U.S.C. 154(b) by 127 days.

(21) Appl. No.: 16/900,308

(22) Filed: Jun. 12, 2020

(65) Prior Publication Data

US 2020/0312642 A1    Oct. 1, 2020

Related U.S. Application Data

(63) Continuation of application No. PCT/IB2018/059982, filed on Dec. 13, 2018.
(Continued)

(51) Int. Cl.
*G01J 1/00* (2006.01)
*H01J 49/00* (2006.01)
(Continued)

(52) U.S. Cl.
CPC ......... *H01J 49/0036* (2013.01); *G01J 3/0264* (2013.01); *G01J 3/28* (2013.01);
(Continued)

(58) Field of Classification Search
CPC ........ H01J 49/0036; H01J 49/06; H01J 49/26; G01J 3/0264; G01J 3/28; G01J 2003/283;
(Continued)

(56) References Cited

U.S. PATENT DOCUMENTS 9,146,213 B2    9/2015   Gorenstein et al.
9,189,595 B2    11/2015  Dai et al.
(Continued)

FOREIGN PATENT DOCUMENTS

JP          5 080945 B2     11/2012
WO       WO 2007/140327    12/2007

OTHER PUBLICATIONS

Hoffmann et al., "Combining peak-and chromatogram-based retention time alignment algorithms for multiple chromatography-mass spectrometry datasets", MBC Bioinformatics, vol. 13, No. 214, 20 pages. (Year: 2012).*
(Continued)

*Primary Examiner* — Kiho Kim
(74) *Attorney, Agent, or Firm* — Womble Bond Dickinson (US) LLP

(57) ABSTRACT

A method, apparatus, and computer-readable storage medium for analyzing component separation/mass spectrometer data for a sample having known characteristic includes analyzing reference ion data for a relationship between ion mass, retention time, and intensity. The analyzed data is added to a repository, wherein each ion therein has an intensity maxima within a characteristic retention time range for a characteristic ion mass. If the reference ion is in the repository, the range is modified according to the characteristic retention time of the reference ion intensity maxima. Based on the known characteristic, an ion expected in the sample is selected from the repository, and sample data is compared to data for the ion selected from the
(Continued)

repository to determine whether the ion is present in the sample. The range in the repository is then modified according to the characteristic retention time of the intensity maxima for the ion present in the sample.

58 Claims, 8 Drawing Sheets

Related U.S. Application Data

(60) Provisional application No. 62/599,403, filed on Dec. 15, 2017.

(51) Int. Cl.
    *G01J 3/02* (2006.01)
    *G01J 3/28* (2006.01)
    *H01J 49/06* (2006.01)
    *H01J 49/26* (2006.01)

(52) U.S. Cl.
    CPC .............. *H01J 49/06* (2013.01); *H01J 49/26* (2013.01); *G01J 2003/283* (2013.01)

(58) Field of Classification Search
    CPC ........... G16C 20/20; G01N 2030/8813; G01N 30/8665; G01N 30/72
    See application file for complete search history.

(56) References Cited

U.S. PATENT DOCUMENTS

| 2009/0179147 | A1 | 7/2009 | Milgram et al. |
| 2015/0369782 | A1* | 12/2015 | Kageyama .......... H01J 49/0036 250/288 |
| 2017/0117122 | A1 | 4/2017 | Dai et al. |
| 2017/0299558 | A1 | 10/2017 | Stevens |

OTHER PUBLICATIONS

International Preliminary Report on Patentability for corresponding International Application No. PCT/IB2018/059982 dated Jun. 16, 2020.

International Search Report and Written Opinion for corresponding International Application No. PCT/IB2018/059982 dated May 3, 2019.

* cited by examiner

METHOD FOR ANALYZING SMALL MOLECULE COMPONENTS OF A COMPLEX MIXTURE, AND ASSOCIATED APPARATUS AND COMPUTER PROGRAM PRODUCT

CROSS-REFERENCE TO RELATED APPLICATIONS

This application is a continuation of International Patent Appl. No. PCT/IB2018/059982, filed Dec. 13, 2018, which International Application was published by the International Bureau in English on Jun. 20, 2019, and which claims priority to U.S. Provisional Appl. No. 62/599,403, filed Dec. 15, 2017, both of which are incorporated by reference herein in their entirety.

BACKGROUND OF THE DISCLOSURE

Field of the Disclosure

The present disclosure relates to the field of analyzing small molecule components in a complex mixture and, more particularly, to a method and associated apparatus and computer program product for analyzing small molecule components of a complex mixture, with such small molecule analysis including metabolomics, which is the study of small molecules produced by an organism's metabolic processes, or other analysis of small molecules produced through metabolism.

Description of Related Art

Metabolomics is the study of the small molecules, or metabolites, contained in a cell, tissue or organ (including fluids) and involved in primary and intermediary metabolism. The term "metabolome" refers to the collection of metabolites present in an organism. The human metabolome encompasses native small molecules (natively biosynthesizeable, non-polymeric compounds) that are participants in general metabolic reactions and that are required for the maintenance, growth and normal function of a cell. Thus, metabolomics is a direct observation of the status of cellular physiology, and may thus be predictive of disease in a given organism. Subtle biochemical changes (including the presence of selected metabolites) are inherent in a given disease. Therefore, the accurate mapping of these changes to known pathways may allow researchers to build a biochemical hypothesis for a disease. Based on this hypothesis, the enzymes and proteins critical to the disease can be uncovered such that disease targets may be identified for treatment with targeted pharmaceutical compounds or other therapy.

Molecular biology techniques for uncovering the biochemical processes underlying disease have been centered on the genome, which consists of the genes that make up DNA, which is transcribed into RNA and then translated to proteins, which then make up the small molecules of the human metabolome. While genomics (study of the DNA-level biochemistry), transcript profiling (study of the RNA-level biochemistry), and proteomics (study of the protein-level biochemistry) are useful for identification of disease pathways, these methods are complicated by the fact that there exist over 25,000 genes, 100,000 to 200,000 RNA transcripts and up to 1,000,000 proteins in human cells. However, it is estimated that there may be as few as 2,500 small molecules in the human metabolome.

Thus, metabolomic technology provides a significant leap beyond genomics, transcript profiling, and/or proteomics. With metabolomics, metabolites and their role in metabolism may be readily identified. In this context, the identification of disease targets may be expedited with greater accuracy relative to other known methods. The collection of metabolomic data for use in identifying disease pathways is generally known in the art, as described generally, for example, in U.S. Pat. Nos. 7,005,255 and 7,329,489 to Metabolon, Inc., each entitled Methods for Drug Discovery, Disease Treatment, and Diagnosis Using Metabolomics. Additional uses for metabolomics data are described therein and include, for example, determining response to a therapeutic agent (i.e., a drug) or other xenobiotics, monitoring drug response, determining drug safety, and drug discovery. However, the collection and sorting of metabolomic data taken from a variety of samples (e.g., from a patient population) consumes large amounts of time and computational power. For example, according to some known metabolomic techniques, spectrometry data for certain samples is collected and plotted in three (or more) dimensions (i.e., sample properties that can be represented along an axis with respect to other sample properties) and stored in an individual file corresponding to each sample. This data is then, by individual file, compared to data corresponding to a plurality of known metabolites in order to identify known metabolites that may be disease targets. The data may also be used for identification of toxic agents and/or drug metabolites. Furthermore, such data may also be used to monitor the effects of xenobiotics and/or used to monitor/measure/identify the xenobiotics and associated metabolites produced by processing (metabolizing) the xenobiotics. However, such conventional "file-based" methods (referring to the individual data file generated for each sample) require the use of large amounts of computing power and memory capacity to handle the screening of large numbers of known metabolites. Furthermore, "file-based" data handling may not lend itself to the compilation of sample population data across a number of samples because, according to known metabolomic data handling techniques, each sample is analyzed independently, without taking into account subtle changes in metabolite composition that may be more readily detectable across a sample population. Furthermore, existing "file-based" method may have other limitations including: limited security and auditability; and poor data set consistency across multiple file copies. In addition, individual files may not support multiple indices (i.e., day collected, sample ID, control vs. treated, drug dose, etc.) such that all files must be scanned when only a particular subset is desired. Such "file-based" methods may thus be of limited assistance in using previously-collected data to facilitate the analysis of data for new samples.

These limitations in current metabolomic data analysis techniques may lead to the discarding of potentially relevant and/or valuable metabolomic data that may be used to identify and classify particular metabolites as disease targets. Specifically, spectrometry data corresponding to a number of samples (such as tissue samples from individual human subjects) generally results in a large data file corresponding to each sample, wherein each data file must then be subjected to an individual screening process with respect to a library of known metabolites. However, conventional systems do not readily allow for the consolidation of spectrometry data from a number of samples for the subjective evaluation of the data generated by the spectrometry processes. Thus, while a single file corresponding to an individual sample may be inconclusive, such data may be more telling if viewed subjectively in a succinct format with respect to other samples within a sample population.

One particular example of a limitation in current metabolomic data analysis techniques involves the identification of a metabolite in each of a plurality of sample. In some instances, the identification of the metabolite involves analyzing the data file of each sample to determine whether an indication (i.e., an intensity peak for a particular sample ion mass or sample component mass, observed at a particular retention time or range or retention times) of that metabolite exists within the respective data files. However, as previously noted, it may be difficult in "file based" data handling methods to verify whether the determined indication is consistent across samples. For example, it may be difficult to determine whether the identified intensity peaks are aligned with respect to retention time across the samples. Further, there may be instances where the indication (e.g., the intensity peak) is not clearly defined within the data file of one or more samples. In those instances, the indication (e.g., the intensity peak) may actually reflect the presence of more than one sample component and, as such, any analysis of those intensity peaks as a whole may be significantly inaccurate. As such, the various assumptions and estimates, which may be difficult to analyze for individual samples when using a file-base data handling method, may result in an inaccurate indication of factors such as the identification and quantity of that metabolite (or a plurality of metabolites) present over/across the plurality of the sample. In this regard, such inaccuracy introduced into a metabolomics analysis at such an early stage may lead to larger inaccuracies in subsequent steps or analyses.

This collection of metabolomics data, as well as other empirical data representing a knowledge base of metabolites including, for example, individual metabolite characteristics, situational metabolite characteristics, and interactional metabolite characteristics, also provides an opportunity for using this trove of data to predict and/or identify metabolites likely to be present in a particular sample, and/or to facilitate validation of the data collected for a particular sample.

Therefore, there exists a need for an improved apparatus and method for solving the technical issues outlined above that are associated with conventional metabolomic data analysis systems. More particularly, there exists a need for an apparatus and method capable of analyzing spectrometry data over/across samples, with the option of, but not the need for, generating a separate data file for each sample. There also exists a need for an apparatus and method capable of allowing a user to subjectively evaluate spectrometry data across a plurality of samples to identify selected metabolites, for allowing the user to verify or otherwise determine the confidence in the identification of the selected metabolites, for allowing the user to examine the data associated with the identification of the selected metabolites, for example, for sorting, grouping, and/or aligning purposes, and for allowing the user to determine additional information related to the identified selected metabolites, for instance, for quality control and consistency verification purposes. There also exists a need for an improved apparatus and method capable of more accurately identifying sample components over/across samples from the acquired spectrometry data. In addition, there exists a need for better implementation of existing metabolomics data, as well as other available metabolomics information, in the metabolomics analysis of subsequent samples.

SUMMARY OF THE DISCLOSURE

The above and other needs are met by aspects of the present disclosure which, in one aspect, provides a method of analyzing data for a sample having a known characteristic, wherein the data for the sample is obtained from a component separation and mass spectrometer system. Such a method comprises analyzing data obtained from the component separation and mass spectrometer system for a reference ion, to determine a relationship between reference ion mass, retention time, and intensity, including intensity as a function of retention time for the reference ion mass, wherein the reference ion has an intensity maxima at a characteristic retention time for the reference ion mass; adding the analyzed data for the reference ion to an ion data repository, wherein each of the ions in the ion data repository has an intensity maxima within a range of characteristic retention times for a characteristic ion mass; modifying, if the reference ion was previously included in the ion data repository, the range of characteristic retention times of the reference ion in the ion data repository, according to the characteristic retention time of the intensity maxima for the reference ion; selecting, via a user interface, one or more ions from the ion data repository expected to be included in the sample based on the known characteristic of the sample; comparing, on a display associated with the user interface, data obtained from the component separation and mass spectrometer system for the sample to data for each of the one or more ions selected from the ion data repository to determine whether any of the one or more ions is present in the sample; and modifying, via the user interface, the range of characteristic retention times of each of the one or more ions determined to be present in the sample, in the data repository, according to the characteristic retention time of the intensity maxima for a respective one of the one or more ions determined to be present in the sample.

Another aspect of the present disclosure provides an apparatus for analyzing data for a sample having a known characteristic, with the data for the sample being obtained from a component separation and mass spectrometer system, wherein the apparatus comprises a processor and a memory storing executable instructions that, in response to execution by the processor, cause the apparatus to at least perform the steps of the method aspect of the present disclosure.

A further aspect of the present disclosure provides a computer program product for analyzing data for a sample having a known characteristic, with the data for the sample being obtained from a component separation and mass spectrometer system, wherein the computer program product comprises at least one non-transitory computer readable storage medium having computer-readable program code stored thereon, the computer-readable program code comprising program code that is executable to at least perform the steps of the method aspect of the present disclosure.

The present disclosure thus includes, without limitation, the following embodiments:

Embodiment 1: A method of analyzing data for a sample having a known characteristic, the data for the sample being obtained from a component separation and mass spectrometer system, said method comprising analyzing data obtained from the component separation and mass spectrometer system for a reference ion, to determine a relationship between reference ion mass, retention time, and intensity, including intensity as a function of retention time for the reference ion mass, the reference ion having an intensity maxima at a characteristic retention time for the reference ion mass; adding the analyzed data for the reference ion to an ion data repository, each of the ions in the ion data repository having an intensity maxima within a range of characteristic retention times for a characteristic ion mass; modifying, if the reference ion was previously included in the ion data repository, the range of characteristic retention times of the reference ion in the ion data repository, according to the characteristic retention time of the intensity maxima for the reference ion; selecting, via a user interface, one or more ions from the ion data repository expected to be included in the sample based on the known characteristic of the sample; comparing, on a display associated with the user interface, data obtained from the component separation and mass spectrometer system for the sample to data for each of the one or more ions selected from the ion data repository to determine whether any of the one or more ions is present in the sample; and modifying, via the user interface, the range of characteristic retention times of each of the one or more ions determined to be present in the sample, in the data repository, according to the characteristic retention time of the intensity maxima for a respective one of the one or more ions determined to be present in the sample.

Embodiment 2: The method of any preceding embodiment, or any combination of preceding embodiments, comprising including the reference ion in the sample.

Embodiment 3: The method of any preceding embodiment, or any combination of preceding embodiments, comprising: analyzing data obtained from the component separation and mass spectrometer system for the sample to determine a relationship between sample ion mass, retention time, and intensity, including intensity as a function of retention time for a selected sample ion mass, the selected sample ion mass being selected via the user interface; selecting, via the user interface, an ion present in the data for the sample, the selected ion having an intensity maxima at a characteristic retention time for the selected sample ion mass; comparing the data for the selected ion to the selected one or more ions in the ion data repository expected to be included in the sample based on the known characteristic of the sample, in order to determine an identity of the selected ion; and modifying the range of characteristic retention times of the ion in the ion data repository corresponding to the selected ion, according to the characteristic retention time of the intensity maxima for the selected ion.

Embodiment 4: The method of any preceding embodiment, or any combination of preceding embodiments, wherein selecting one or more ions from the ion data repository expected to be included in the sample based on the known characteristic of the sample comprises querying the ion data repository via the user interface to select the one or more ions therefrom based upon a retention time of an intensity maxima of a selected ion from the data for the sample in relation to the range of characteristic retention times of the intensity maxima of the one or more ions in the ion data repository.

Embodiment 5: The method of any preceding embodiment, or any combination of preceding embodiments, wherein the sample comprises a plurality of samples in a sample run, and wherein selecting one or more ions from the ion data repository expected to be included in the sample based on the known characteristic of the sample comprises selecting the one or more ions from the ion data repository in relation to ions determined to be present in a first one of the plurality of samples, the selected one or more ions related to ions determined to be present in a first one of the plurality of samples being used for comparison to the data for a remainder of the samples in the sample run.

Embodiment 6: The method of any preceding embodiment, or any combination of preceding embodiments, wherein comparing, on a display associated with the user interface, data obtained from the component separation and mass spectrometer system for the sample to data for each of the one or more ions selected from the ion data repository comprises comparing, on the display, a two dimensional plot of intensity as a function of retention time for the sample to a two dimensional plot of intensity as a function of retention time for each of the one or more ions selected from the ion data repository so as to provide a visual indication of intensity maxima therebetween for determining whether any of the one or more ions is present in the sample.

Embodiment 7: The method of any preceding embodiment, or any combination of preceding embodiments, wherein modifying, if the reference ion was previously included in the ion data repository, the range of characteristic retention times of the reference ion in the ion data repository, according to the characteristic retention time of the intensity maxima for the reference ion comprises reducing the range of characteristic retention times if the characteristic retention time of the intensity maxima for the reference ion is within the range of characteristic retention times; and determining whether any data deviation factors in the component separation and mass spectrometer system require consideration if the characteristic retention time of the intensity maxima for the reference ion is outside the range of characteristic retention times.

Embodiment 8: The method of any preceding embodiment, or any combination of preceding embodiments, wherein the relationship between reference ion mass, retention time, and intensity, includes intensity as a function of the reference ion mass for a selected retention time, wherein the adding step comprises adding the analyzed data for the reference ion to an ion data repository such that each of the ions in the ion data repository have the intensity maxima within a range of characteristic ion masses for a characteristic retention time, and wherein the modifying step comprises modifying, if the reference ion was previously included in the ion data repository, the range of characteristic ion masses of the reference ion in the ion data repository, according to the characteristic ion mass of the intensity maxima for the reference ion.

Embodiment 9: The method of any preceding embodiment, or any combination of preceding embodiments, wherein selecting one or more ions from the ion data repository comprises comparing the known characteristic to empirical data included in the ion data repository, the empirical data including relational information between known characteristics and ions, and determining therefrom the one or more ions corresponding to the known characteristic of the sample.

Embodiment 10: The method of any preceding embodiment, or any combination of preceding embodiments, wherein, after comparing data for the sample to data for the one or more ions from the ion data repository and determining whether any of the one or more ions is present in the sample, the method comprises adding empirical data associated with the sample to the ion data repository in relation to the any of the one or more ions determined to be present in the sample.

Embodiment 11: The method of any preceding embodiment, or any combination of preceding embodiments, comprising analyzing data obtained from the component separation and mass spectrometer system for an anchor sample, the anchor sample being defined as a consistent, previously-characterized sample, to determine a component ion of the anchor sample and a relationship between component ion mass, retention time, and intensity, including intensity as a function of retention time for the component ion mass, the component ion having an intensity maxima at a characteristic component ion retention time for the component ion mass.

Embodiment 12: The method of any preceding embodiment, or any combination of preceding embodiments, wherein the component ion mass is substantially equal to the characteristic ion mass of one of the one or more ions determined to be in the sample, and the method comprises comparing the intensity maxima for the component ion at the characteristic component ion retention time, to the intensity maxima for the one of the one or more ions determined to be in the sample at the characteristic retention time, wherein if the intensity maxima for the component ion and the one of the one or more ions determined to be in the sample are substantially similar, then the one of the one or more ions determined to be in the sample is designated as an artifact ion in the sample.

Embodiment 13: The method of any preceding embodiment, or any combination of preceding embodiments, wherein the anchor sample comprises water.

Embodiment 14: The method of any preceding embodiment, or any combination of preceding embodiments, wherein the sample comprises a plurality of samples in a sample run, wherein the method comprises analyzing the plurality of samples in the sample run to determine a presence of one of the one or more ions from the ion data repository determined to be present in a first one of the plurality of samples, across the plurality of samples, and wherein if a threshold quantity of the samples in the plurality of samples does not include the one of the one or more ions from the ion data repository determined to be present in the first one of the plurality of samples, then the one of the one or more ions determined to be present in the first one of the plurality of samples is designated as sparse ion in the plurality of samples.

Embodiment 15: The method of any preceding embodiment, or any combination of preceding embodiments, wherein the sample comprises a plurality of samples in a sample run, and wherein the method comprises analyzing data obtained from the component separation and mass spectrometer system for each sample to determine a relationship between sample ion mass, retention time, and intensity, including intensity as a function of retention time for a selected sample ion mass, the selected sample ion mass being selected via the user interface; analyzing the intensity as the function of retention time for the selected sample ion mass for each of the samples, across the plurality of samples, to identify an intensity maxima within a predicted range of retention times for each sample, the predicted range of retention times including an expected intensity maxima retention time therein for the selected sample ion mass; identifying, for each sample, an actual retention time of the intensity maxima in relation to the expected intensity maxima retention time; and determining whether the actual retention times of the intensity maxima of two or more consecutive samples of the plurality of samples in the sample run demonstrate an identifiable pattern with respect to the expected intensity maxima retention time.

Embodiment 16: The method of any preceding embodiment, or any combination of preceding embodiments, wherein the identifiable pattern of the actual retention times of the intensity maxima of the two or more consecutive samples, with respect to the expected intensity maxima retention time, comprises a shift wherein the actual retention times of the intensity maxima are substantially consistently offset from the expected intensity maxima retention time, or a drift wherein the actual retention times of the intensity maxima are offset by a non-constant function from the expected intensity maxima retention time, and wherein the method comprises correcting the offset of the actual retention time of the intensity maxima of each of the plurality of samples in the sample run according to the identifiable pattern.

Embodiment 17: The method of any preceding embodiment, or any combination of preceding embodiments, wherein the identifiable pattern of the actual retention times of the intensity maxima of the two or more consecutive samples, with respect to the expected intensity maxima retention time, comprises an offset from the expected intensity maxima retention time, the offset differing between two subsets of two or more consecutive samples in the sample run, and wherein the method comprises correcting the offset of the actual retention times of the intensity maxima of each of the plurality of samples in the sample run according to the identifiable pattern of one of the two subsets having a majority of the samples in the sample run.

Embodiment 18: The method of any preceding embodiment, or any combination of preceding embodiments, wherein, if comparing data obtained from the component separation and mass spectrometer system for the sample to data for each of the one or more ions selected from the ion data repository to determine whether any of the one or more ions is present in the sample results in none of the one or more ions being present in the sample, then the method comprises resolving an instrument error associated with the component separation and mass spectrometer system and re-running the sample through the component separation and mass spectrometer system to obtain replacement data for the sample.

Embodiment 19: The method of any preceding embodiment, or any combination of preceding embodiments, comprising displaying, on the display associated with the user interface, the corrected offset of the actual retention time of the intensity maxima of each of the plurality of samples in the sample run according to the identifiable pattern to provide a visualization of the corrected actual retention time of the intensity maxima of each of the plurality of samples across the plurality of samples in the sample run.

Embodiment 20: An apparatus for analyzing data for a sample having a known characteristic, the data for the sample being obtained from a component separation and mass spectrometer system, the apparatus comprising a processor and a memory storing executable instructions that, in response to execution by the processor, cause the apparatus to at least perform the steps of analyzing data obtained from the component separation and mass spectrometer system for a reference ion, to determine a relationship between reference ion mass, retention time, and intensity, including intensity as a function of retention time for the reference ion mass, the reference ion having an intensity maxima at a characteristic retention time for the reference ion mass; adding the analyzed data for the reference ion to an ion data repository, each of the ions in the ion data repository having an intensity maxima within a range of characteristic retention times for a characteristic ion mass; modifying, if the reference ion was previously included in the ion data repository, the range of characteristic retention times of the reference ion in the ion data repository, according to the characteristic retention time of the intensity maxima for the reference ion; selecting, via a user interface associated with the apparatus, one or more ions from the ion data repository expected to be included in the sample based on the known characteristic of the sample; comparing, on a display associated with the user interface, data obtained from the component separation and mass spectrometer system for the sample to data for each of the one or more ions selected from the ion data repository to determine whether any of the one or more ions is present in the sample; and modifying, via the user interface, the range of characteristic retention times of each of the one or more ions determined to be present in the sample, in the data repository, according to the characteristic retention time of the intensity maxima for a respective one of the one or more ions determined to be present in the sample.

Embodiment 21: The apparatus of any preceding embodiment, or any combination of preceding embodiments, wherein the reference ion is included in the sample.

Embodiment 22: The apparatus of any preceding embodiment, or any combination of preceding embodiments, wherein the memory stores executable instructions that, in response to execution by the processor, cause the apparatus to further perform the steps of analyzing data obtained from the component separation and mass spectrometer system for the sample to determine a relationship between sample ion mass, retention time, and intensity, including intensity as a function of retention time for a selected sample ion mass, the selected sample ion mass being selected via the user interface; selecting, via the user interface, an ion present in the data for the sample, the selected ion having an intensity maxima at a characteristic retention time for the selected sample ion mass; comparing the data for the selected ion to the selected one or more ions in the ion data repository expected to be included in the sample based on the known characteristic of the sample, in order to determine an identity of the selected ion; and modifying the range of characteristic retention times of the ion in the ion data repository corresponding to the selected ion, according to the characteristic retention time of the intensity maxima for the selected ion.

Embodiment 23: The apparatus of any preceding embodiment, or any combination of preceding embodiments, wherein the memory stores executable instructions that, in response to execution by the processor, cause the apparatus to further perform the step of querying the ion data repository via the user interface to select the one or more ions therefrom based upon a retention time of an intensity maxima of a selected ion from the data for the sample in relation to the range of characteristic retention times of the intensity maxima of the one or more ions in the ion data repository.

Embodiment 24: The apparatus of any preceding embodiment, or any combination of preceding embodiments, wherein the sample comprises a plurality of samples in a sample run, and wherein the memory stores executable instructions that, in response to execution by the processor, cause the apparatus to further perform the step of selecting the one or more ions from the ion data repository in relation to ions determined to be present in a first one of the plurality of samples, the selected one or more ions related to ions determined to be present in a first one of the plurality of samples being used for comparison to the data for a remainder of the samples in the sample run.

Embodiment 25: The apparatus of any preceding embodiment, or any combination of preceding embodiments, wherein the memory stores executable instructions that, in response to execution by the processor, cause the apparatus to further perform the step of comparing, on the display, a two dimensional plot of intensity as a function of retention time for the sample to a two dimensional plot of intensity as a function of retention time for each of the one or more ions selected from the ion data repository so as to provide a visual indication of intensity maxima therebetween for determining whether any of the one or more ions is present in the sample.

Embodiment 26: The apparatus of any preceding embodiment, or any combination of preceding embodiments, wherein the memory stores executable instructions that, in response to execution by the processor, cause the apparatus to further perform the steps of reducing the range of characteristic retention times if the characteristic retention time of the intensity maxima for the reference ion is within the range of characteristic retention times; and determining whether any data deviation factors in the component separation and mass spectrometer system require consideration if the characteristic retention time of the intensity maxima for the reference ion is outside the range of characteristic retention times.

Embodiment 27: The apparatus of any preceding embodiment, or any combination of preceding embodiments, wherein the relationship between reference ion mass, retention time, and intensity, includes intensity as a function of the reference ion mass for a selected retention time, and wherein the memory stores executable instructions that, in response to execution by the processor, cause the apparatus to further perform the steps of adding the analyzed data for the reference ion to an ion data repository such that each of the ions in the ion data repository have the intensity maxima within a range of characteristic ion masses for a characteristic retention time; and modifying, if the reference ion was previously included in the ion data repository, the range of characteristic ion masses of the reference ion in the ion data repository, according to the characteristic ion mass of the intensity maxima for the reference ion.

Embodiment 28: The apparatus of any preceding embodiment, or any combination of preceding embodiments, wherein the memory stores executable instructions that, in response to execution by the processor, cause the apparatus to further perform the steps of comparing the known characteristic to empirical data included in the ion data repository, the empirical data including relational information between known characteristics and ions; and determining therefrom the one or more ions corresponding to the known characteristic of the sample.

Embodiment 29: The apparatus of any preceding embodiment, or any combination of preceding embodiments, wherein the memory stores executable instructions that, in response to execution by the processor, cause the apparatus to further perform the step of adding empirical data associated with the sample to the ion data repository in relation to the any of the one or more ions determined to be present in the sample, after comparing data for the sample to data for the one or more ions from the ion data repository and determining whether any of the one or more ions is present in the sample.

Embodiment 30: The apparatus of any preceding embodiment, or any combination of preceding embodiments, wherein the memory stores executable instructions that, in response to execution by the processor, cause the apparatus to further perform the step of analyzing data obtained from the component separation and mass spectrometer system for an anchor sample, the anchor sample being defined as a consistent, previously-characterized sample, to determine a component ion of the anchor sample and a relationship between component ion mass, retention time, and intensity, including intensity as a function of retention time for the component ion mass, the component ion having an intensity maxima at a characteristic component ion retention time for the component ion mass.

Embodiment 31: The apparatus of any preceding embodiment, or any combination of preceding embodiments, wherein the component ion mass is substantially equal to the characteristic ion mass of one of the one or more ions determined to be in the sample, and wherein the memory stores executable instructions that, in response to execution by the processor, cause the apparatus to further perform the step of comparing the intensity maxima for the component ion at the characteristic component ion retention time, to the intensity maxima for the one of the one or more ions determined to be in the sample at the characteristic retention time, wherein if the intensity maxima for the component ion and the one of the one or more ions determined to be in the sample are substantially similar, then the one of the one or more ions determined to be in the sample is designated as an artifact ion in the sample.

Embodiment 32: The apparatus of any preceding embodiment, or any combination of preceding embodiments, wherein the anchor sample comprises water.

Embodiment 33: The apparatus of any preceding embodiment, or any combination of preceding embodiments, wherein the sample comprises a plurality of samples in a sample run, and wherein the memory stores executable instructions that, in response to execution by the processor, cause the apparatus to further perform the step of analyzing the plurality of samples in the sample run to determine a presence of one of the one or more ions from the ion data repository determined to be present in a first one of the plurality of samples, across the plurality of samples, wherein if a threshold quantity of the samples in the plurality of samples does not include the one of the one or more ions from the ion data repository determined to be present in the first one of the plurality of samples, then the one of the one or more ions determined to be present in the first one of the plurality of samples is designated as sparse ion in the plurality of samples.

Embodiment 34: The apparatus of any preceding embodiment, or any combination of preceding embodiments, wherein the sample comprises a plurality of samples in a sample run, and wherein the memory stores executable instructions that, in response to execution by the processor, cause the apparatus to further perform the steps of analyzing data obtained from the component separation and mass spectrometer system for each sample to determine a relationship between sample ion mass, retention time, and intensity, including intensity as a function of retention time for a selected sample ion mass, the selected sample ion mass being selected via the user interface; analyzing the intensity as the function of retention time for the selected sample ion mass for each of the samples, across the plurality of samples, to identify an intensity maxima within a predicted range of retention times for each sample, the predicted range of retention times including an expected intensity maxima retention time therein for the selected sample ion mass; identifying, for each sample, an actual retention time of the intensity maxima in relation to the expected intensity maxima retention time; and determining whether the actual retention times of the intensity maxima of two or more consecutive samples of the plurality of samples in the sample run demonstrate an identifiable pattern with respect to the expected intensity maxima retention time.

Embodiment 35: The apparatus of any preceding embodiment, or any combination of preceding embodiments, wherein the identifiable pattern of the actual retention times of the intensity maxima of the two or more consecutive samples, with respect to the expected intensity maxima retention time, comprises a shift wherein the actual retention times of the intensity maxima are substantially consistently offset from the expected intensity maxima retention time, or a drift wherein the actual retention times of the intensity maxima are offset by a non-constant function from the expected intensity maxima retention time, and wherein the memory stores executable instructions that, in response to execution by the processor, cause the apparatus to further perform the step of correcting the offset of the actual retention time of the intensity maxima of each of the plurality of samples in the sample run according to the identifiable pattern.

Embodiment 36: The apparatus of any preceding embodiment, or any combination of preceding embodiments, wherein the identifiable pattern of the actual retention times of the intensity maxima of the two or more consecutive samples, with respect to the expected intensity maxima retention time, comprises an offset from the expected intensity maxima retention time, the offset differing between two subsets of two or more consecutive samples in the sample run, and wherein the memory stores executable instructions that, in response to execution by the processor, cause the apparatus to further perform the step of correcting the offset of the actual retention times of the intensity maxima of each of the plurality of samples in the sample run according to the identifiable pattern of one of the two subsets having a majority of the samples in the sample run.

Embodiment 37: The apparatus of any preceding embodiment, or any combination of preceding embodiments, wherein, if comparing data obtained from the component separation and mass spectrometer system for the sample to data for each of the one or more ions selected from the ion data repository to determine whether any of the one or more ions is present in the sample results in none of the one or more ions being present in the sample, the memory stores executable instructions that, in response to execution by the processor, then cause the apparatus to further perform the step of resolving an instrument error associated with the component separation and mass spectrometer system and re-running the sample through the component separation and mass spectrometer system to obtain replacement data for the sample.

Embodiment 38: The apparatus of any preceding embodiment, or any combination of preceding embodiments, wherein the memory stores executable instructions that, in response to execution by the processor, cause the apparatus to further perform the step of displaying, on the display associated with the user interface, the corrected offset of the actual retention time of the intensity maxima of each of the plurality of samples in the sample run according to the identifiable pattern to provide a visualization of the corrected actual retention time of the intensity maxima of each of the plurality of samples across the plurality of samples in the sample run.

Embodiment 39: A computer program product for analyzing data for a sample having a known characteristic, the data for the sample being obtained from a component separation and mass spectrometer system, the computer program product comprising at least one non-transitory computer readable storage medium having computer-readable program code stored thereon, the computer-readable program code comprising program code for performing the steps of analyzing data obtained from the component separation and mass spectrometer system for a reference ion, to determine a relationship between reference ion mass, retention time, and intensity, including intensity as a function of retention time for the reference ion mass, the reference ion having an intensity maxima at a characteristic retention time for the reference ion mass; adding the analyzed data for the reference ion to an ion data repository, each of the ions in the ion data repository having an intensity maxima within a range of characteristic retention times for a characteristic ion mass; modifying, if the reference ion was previously included in the ion data repository, the range of characteristic retention times of the reference ion in the ion data repository, according to the characteristic retention time of the intensity maxima for the reference ion; selecting, via a user interface associated with the apparatus, one or more ions from the ion data repository expected to be included in the sample based on the known characteristic of the sample; comparing, on a display associated with the user interface, data obtained from the component separation and mass spectrometer system for the sample to data for each of the one or more ions selected from the ion data repository to determine whether any of the one or more ions is present in the sample; and modifying, via the user interface, the range of characteristic retention times of each of the one or more ions determined to be present in the sample, in the data repository, according to the characteristic retention time of the intensity maxima for a respective one of the one or more ions determined to be present in the sample.

Embodiment 40: The computer program product of any preceding embodiment, or any combination of preceding embodiments, wherein the reference ion is included in the sample.

Embodiment 41: The computer program product of any preceding embodiment, or any combination of preceding embodiments, wherein the computer program product comprises program code for analyzing data obtained from the component separation and mass spectrometer system for the sample to determine a relationship between sample ion mass, retention time, and intensity, including intensity as a function of retention time for a selected sample ion mass, the selected sample ion mass being selected via the user interface; selecting, via the user interface, an ion present in the data for the sample, the selected ion having an intensity maxima at a characteristic retention time for the selected sample ion mass; comparing the data for the selected ion to the selected one or more ions in the ion data repository expected to be included in the sample based on the known characteristic of the sample, in order to determine an identity of the selected ion; and modifying the range of characteristic retention times of the ion in the ion data repository corresponding to the selected ion, according to the characteristic retention time of the intensity maxima for the selected ion.

Embodiment 42: The computer program product of any preceding embodiment, or any combination of preceding embodiments, wherein the computer program product comprises program code for querying the ion data repository via the user interface to select the one or more ions therefrom based upon a retention time of an intensity maxima of a selected ion from the data for the sample in relation to the range of characteristic retention times of the intensity maxima of the one or more ions in the ion data repository.

Embodiment 43: The computer program product of any preceding embodiment, or any combination of preceding embodiments, wherein the sample comprises a plurality of samples in a sample run, and wherein the computer program product comprises program code for selecting the one or more ions from the ion data repository in relation to ions determined to be present in a first one of the plurality of samples, the selected one or more ions related to ions determined to be present in a first one of the plurality of samples being used for comparison to the data for a remainder of the samples in the sample run.

Embodiment 44: The computer program product of any preceding embodiment, or any combination of preceding embodiments, wherein the computer program product comprises program code for comparing a two dimensional plot of intensity as a function of retention time for the sample to a two dimensional plot of intensity as a function of retention time for each of the one or more ions selected from the ion data repository so as to provide a visual indication of intensity maxima therebetween for determining whether any of the one or more ions is present in the sample.

Embodiment 45: The computer program product of any preceding embodiment, or any combination of preceding embodiments, wherein the computer program product comprises program code for comparing, on the display, a two dimensional plot of intensity as a function of retention time for the sample to a two dimensional plot of intensity as a function of retention time for each of the one or more ions selected from the ion data repository so as to provide a visual indication of intensity maxima therebetween for determining whether any of the one or more ions is present in the sample.

Embodiment 46: The computer program product of any preceding embodiment, or any combination of preceding embodiments, wherein the computer program product comprises program code for modifying, if the reference ion was previously included in the ion data repository, the range of characteristic retention times of the reference ion in the ion data repository, according to the characteristic retention time of the intensity maxima for the reference ion comprises reducing the range of characteristic retention times if the characteristic retention time of the intensity maxima for the reference ion is within the range of characteristic retention times; and determining whether any data deviation factors in the component separation and mass spectrometer system require consideration if the characteristic retention time of the intensity maxima for the reference ion is outside the range of characteristic retention times.

Embodiment 47: The computer program product of any preceding embodiment, or any combination of preceding embodiments, wherein the relationship between reference ion mass, retention time, and intensity, includes intensity as a function of the reference ion mass for a selected retention time, and wherein the computer program product comprises program code for adding the analyzed data for the reference ion to an ion data repository such that each of the ions in the ion data repository have the intensity maxima within a range of characteristic ion masses for a characteristic retention time; and modifying, if the reference ion was previously included in the ion data repository, the range of characteristic ion masses of the reference ion in the ion data repository, according to the characteristic ion mass of the intensity maxima for the reference ion.

Embodiment 48: The computer program product of any preceding embodiment, or any combination of preceding embodiments, wherein the computer program product comprises program code for comparing the known characteristic to empirical data included in the ion data repository, the empirical data including relational information between known characteristics and ions; and determining therefrom the one or more ions corresponding to the known characteristic of the sample.

Embodiment 49: The computer program product of any preceding embodiment, or any combination of preceding embodiments, wherein, after comparing data for the sample to data for the one or more ions from the ion data repository and determining whether any of the one or more ions is present in the sample, the computer program product comprises program code for adding empirical data associated with the sample to the ion data repository in relation to the any of the one or more ions determined to be present in the sample.

Embodiment 50: The computer program product of any preceding embodiment, or any combination of preceding embodiments, wherein the computer program product comprises program code for analyzing data obtained from the component separation and mass spectrometer system for an anchor sample, the anchor sample being defined as a consistent, previously-characterized sample, to determine a component ion of the anchor sample and a relationship between component ion mass, retention time, and intensity, including intensity as a function of retention time for the component ion mass, the component ion having an intensity maxima at a characteristic component ion retention time for the component ion mass.

Embodiment 51: The computer program product of any preceding embodiment, or any combination of preceding embodiments, wherein the component ion mass is substantially equal to the characteristic ion mass of one of the one or more ions determined to be in the sample, and wherein the computer program product comprises program code for comparing the intensity maxima for the component ion at the characteristic component ion retention time, to the intensity maxima for the one of the one or more ions determined to be in the sample at the characteristic retention time, wherein if the intensity maxima for the component ion and the one of the one or more ions determined to be in the sample are substantially similar, then the one of the one or more ions determined to be in the sample is designated as an artifact ion in the sample.

Embodiment 52: The computer program product of any preceding embodiment, or any combination of preceding embodiments, wherein the anchor sample comprises water.

Embodiment 53: The computer program product of any preceding embodiment, or any combination of preceding embodiments, wherein the sample comprises a plurality of samples in a sample run, and wherein the computer program product comprises program code for analyzing the plurality of samples in the sample run to determine a presence of one of the one or more ions from the ion data repository determined to be present in a first one of the plurality of samples, across the plurality of samples, wherein if a threshold quantity of the samples in the plurality of samples does not include the one of the one or more ions from the ion data repository determined to be present in the first one of the plurality of samples, then the one of the one or more ions determined to be present in the first one of the plurality of samples is designated as sparse ion in the plurality of samples.

Embodiment 54: The computer program product of any preceding embodiment, or any combination of preceding embodiments, wherein the sample comprises a plurality of samples in a sample run, and wherein the computer program product comprises program code for analyzing data obtained from the component separation and mass spectrometer system for each sample to determine a relationship between sample ion mass, retention time, and intensity, including intensity as a function of retention time for a selected sample ion mass, the selected sample ion mass being selected via the user interface; analyzing the intensity as the function of retention time for the selected sample ion mass for each of the samples, across the plurality of samples, to identify an intensity maxima within a predicted range of retention times for each sample, the predicted range of retention times including an expected intensity maxima retention time therein for the selected sample ion mass; identifying, for each sample, an actual retention time of the intensity maxima in relation to the expected intensity maxima retention time; and determining whether the actual retention times of the intensity maxima of two or more consecutive samples of the plurality of samples in the sample run demonstrate an identifiable pattern with respect to the expected intensity maxima retention time.

Embodiment 55: The computer program product of any preceding embodiment, or any combination of preceding embodiments, wherein the identifiable pattern of the actual retention times of the intensity maxima of the two or more consecutive samples, with respect to the expected intensity maxima retention time, comprises a shift wherein the actual retention times of the intensity maxima are substantially consistently offset from the expected intensity maxima retention time, or a drift wherein the actual retention times of the intensity maxima are offset by a non-constant function from the expected intensity maxima retention time, and wherein the computer program product comprises program code for correcting the offset of the actual retention time of the intensity maxima of each of the plurality of samples in the sample run according to the identifiable pattern.

Embodiment 56: The computer program product of any preceding embodiment, or any combination of preceding embodiments, wherein the identifiable pattern of the actual retention times of the intensity maxima of the two or more consecutive samples, with respect to the expected intensity maxima retention time, comprises an offset from the expected intensity maxima retention time, the offset differing between two subsets of two or more consecutive samples in the sample run, and wherein the computer program product comprises program code for correcting the offset of the actual retention times of the intensity maxima of each of the plurality of samples in the sample run according to the identifiable pattern of one of the two subsets having a majority of the samples in the sample run.

Embodiment 57: The computer program product of any preceding embodiment, or any combination of preceding embodiments, wherein, if comparing data obtained from the component separation and mass spectrometer system for the sample to data for each of the one or more ions selected from the ion data repository to determine whether any of the one or more ions is present in the sample results in none of the one or more ions being present in the sample, the computer program product comprises program code for then resolving an instrument error associated with the component separation and mass spectrometer system and re-running the sample through the component separation and mass spectrometer system to obtain replacement data for the sample.

Embodiment 58: The computer program product of any preceding embodiment, or any combination of preceding embodiments, wherein the computer program product comprises program code for displaying, on the display associated with the user interface, the corrected offset of the actual retention time of the intensity maxima of each of the plurality of samples in the sample run according to the identifiable pattern to provide a visualization of the corrected actual retention time of the intensity maxima of each of the plurality of samples across the plurality of samples in the sample run.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure or recited in any one or more of the claims, regardless of whether such features or elements are expressly combined or otherwise recited in a specific embodiment description or claim herein. This disclosure is intended to be read holistically such that any separable features or elements of the disclosure, in any of its aspects and embodiments, should be viewed as intended to be combinable, unless the context of the disclosure clearly dictates otherwise.

Thus, the apparatuses, methods, and computer program products for analyzing data for a sample having a known characteristic, with the data being obtained from a component separation and mass spectrometer system and according to aspects of the present disclosure provide these and other advantages, as detailed further herein. Importantly, these advantages include the ability to dynamically and autonomously identify and verify ions, compounds or other components present in a sample having a known characteristic, with increased quality and consistency of analysis results. These advantages also include the capability of increasing curation/verification speed for identified ions, compounds or components of the sample, while lowering the manual manipulation of data required for verification/curation, for example, by providing a visual verification process.

BRIEF DESCRIPTION OF THE SEVERAL VIEWS OF THE DRAWINGS

Figure 1:
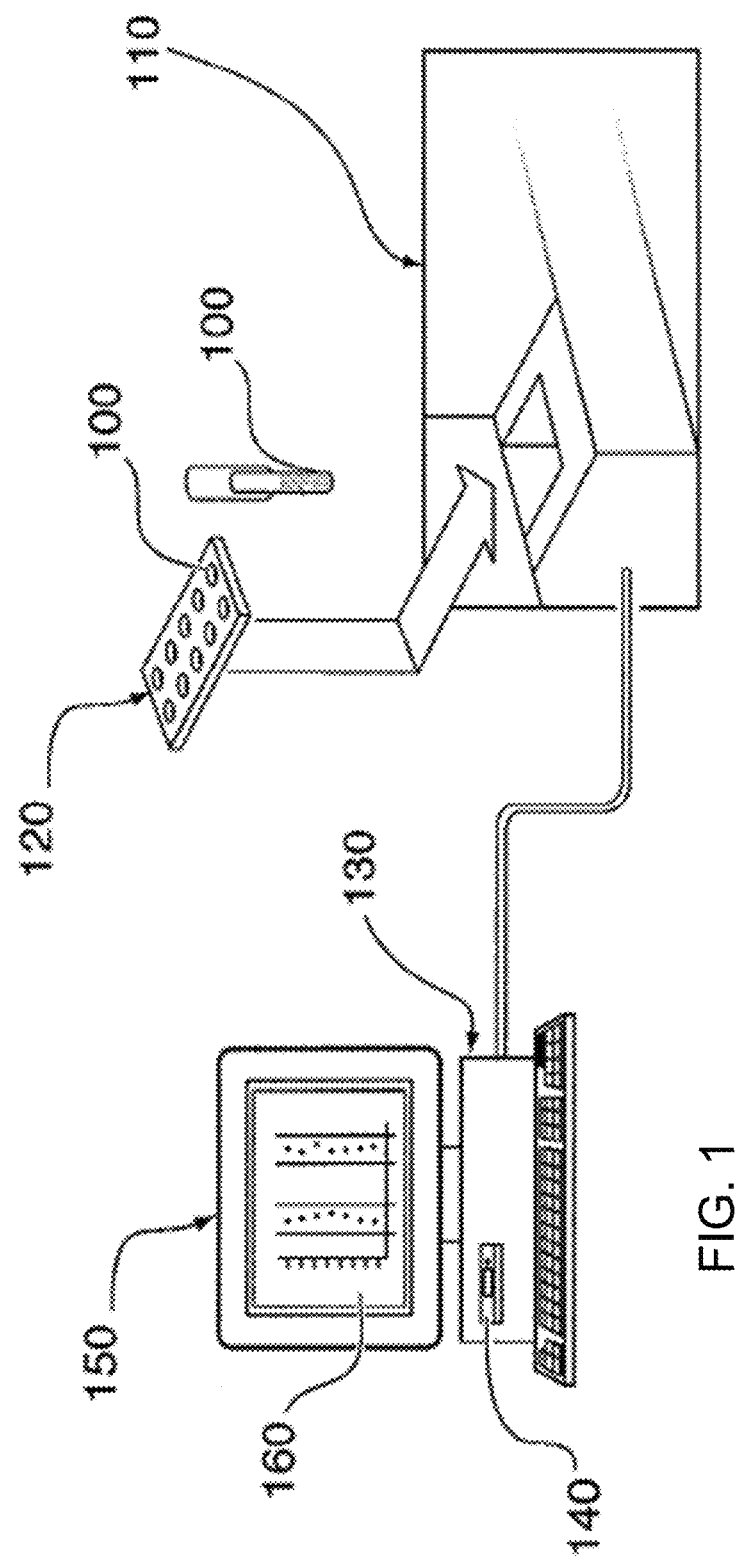
Figure 2:
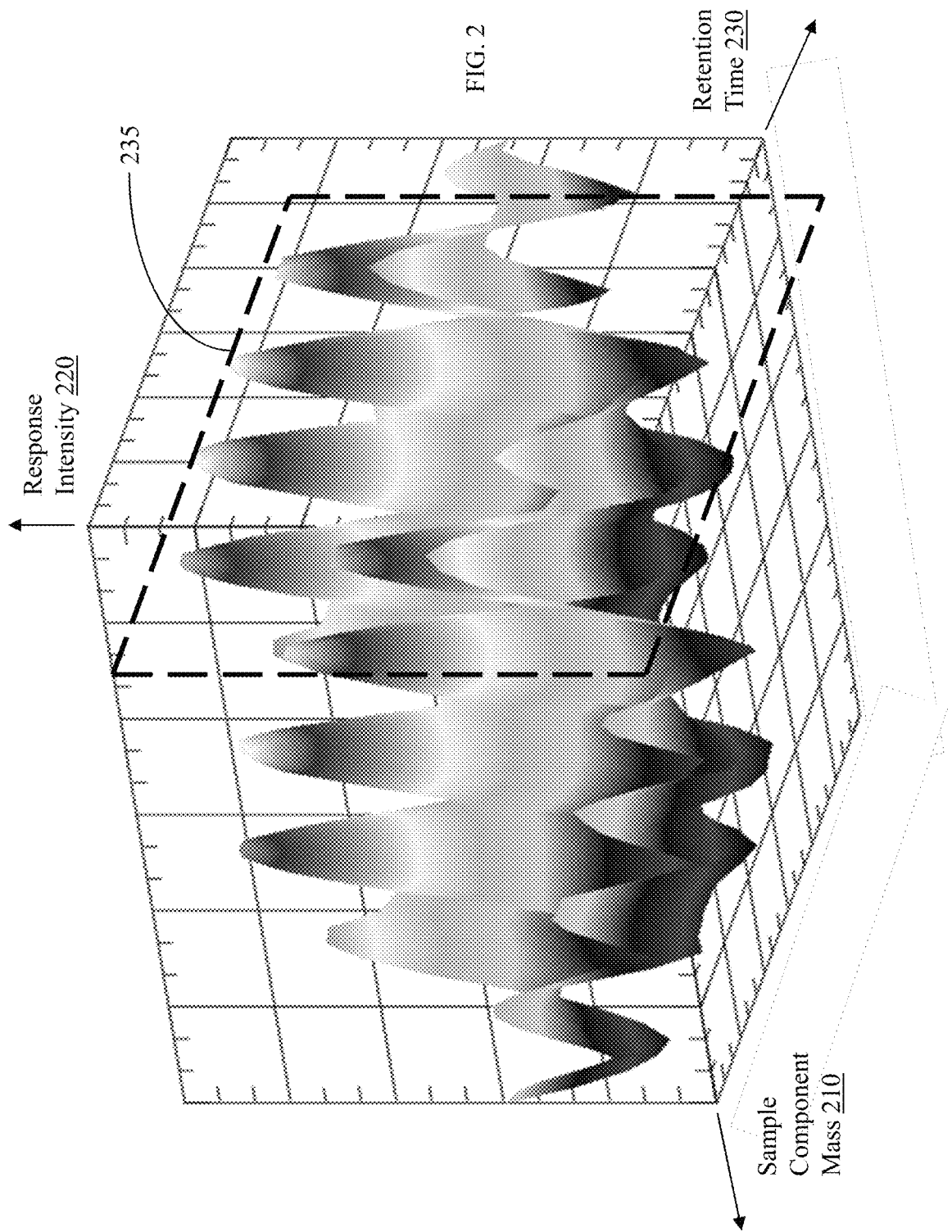
Figure 3:
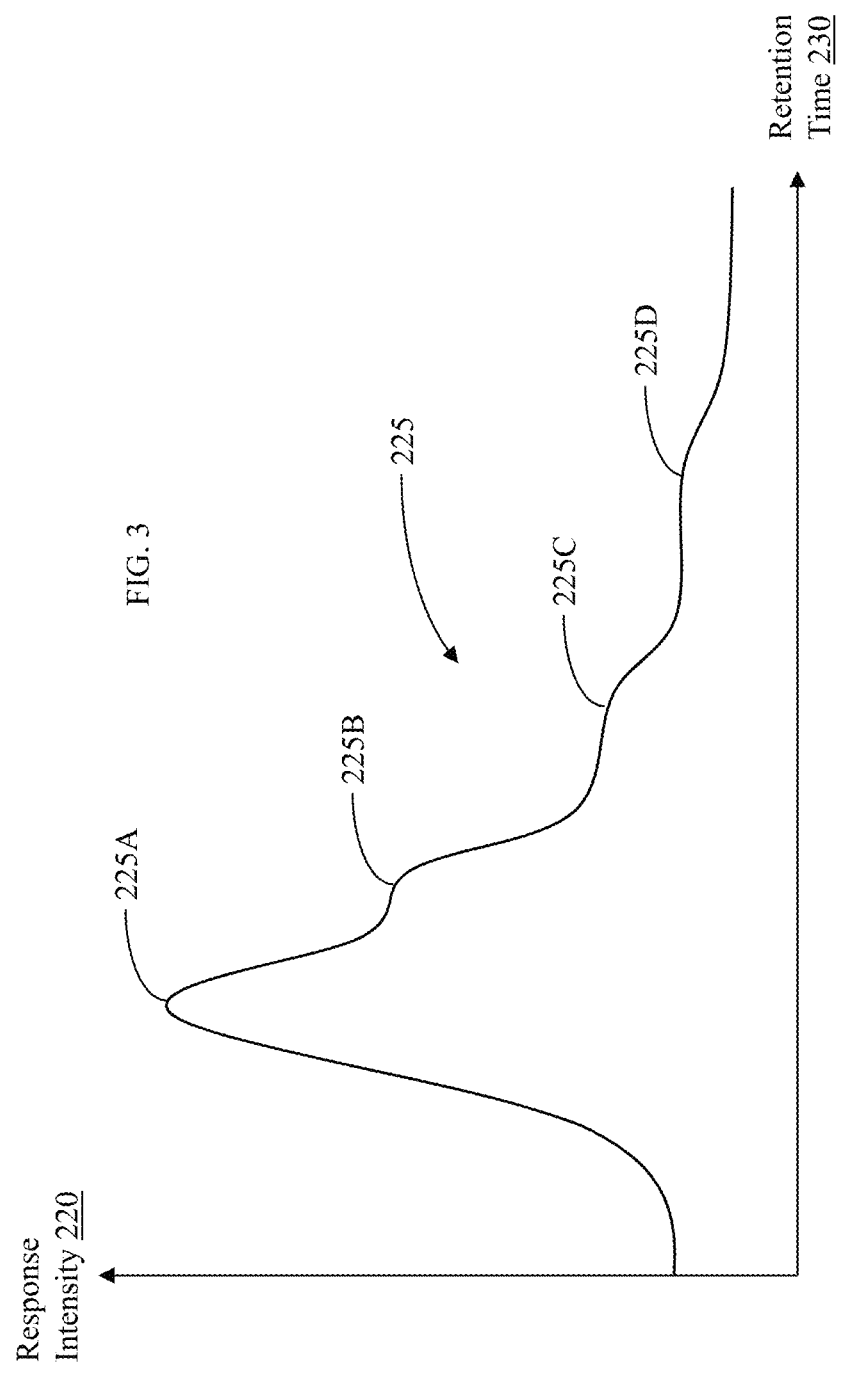
Figure 4:
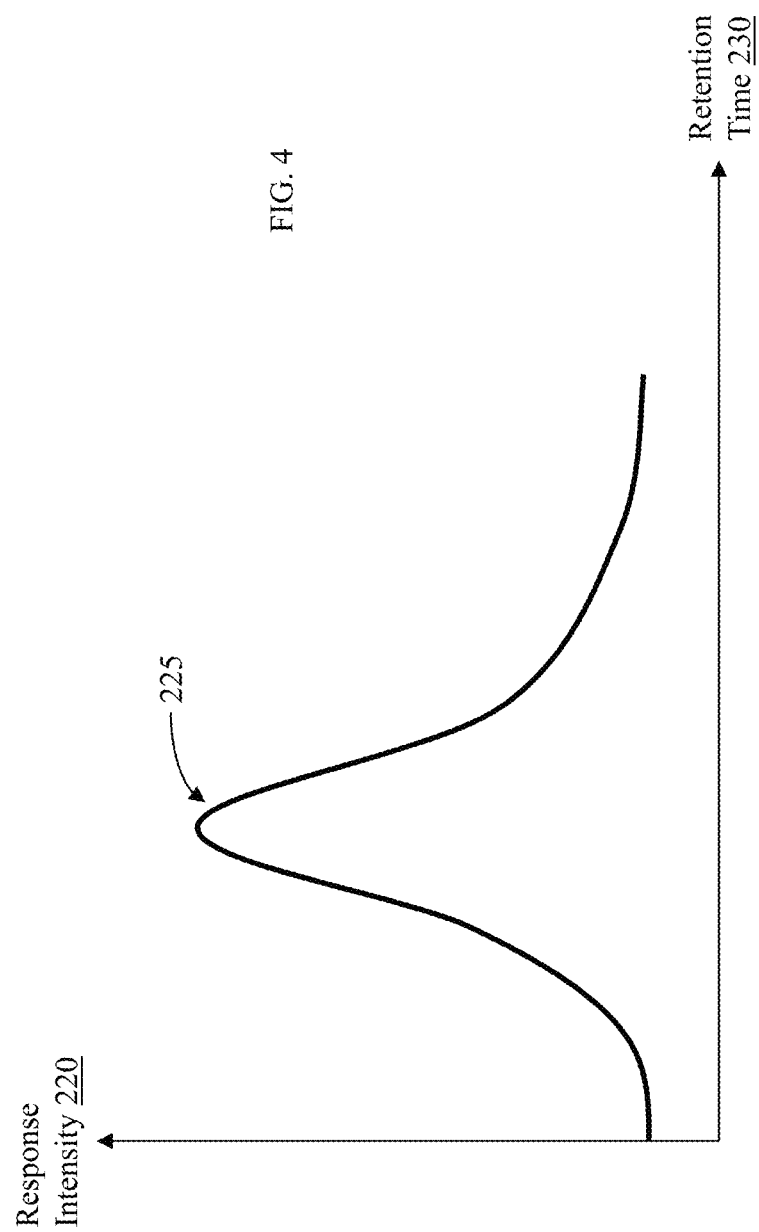
Figure 5:
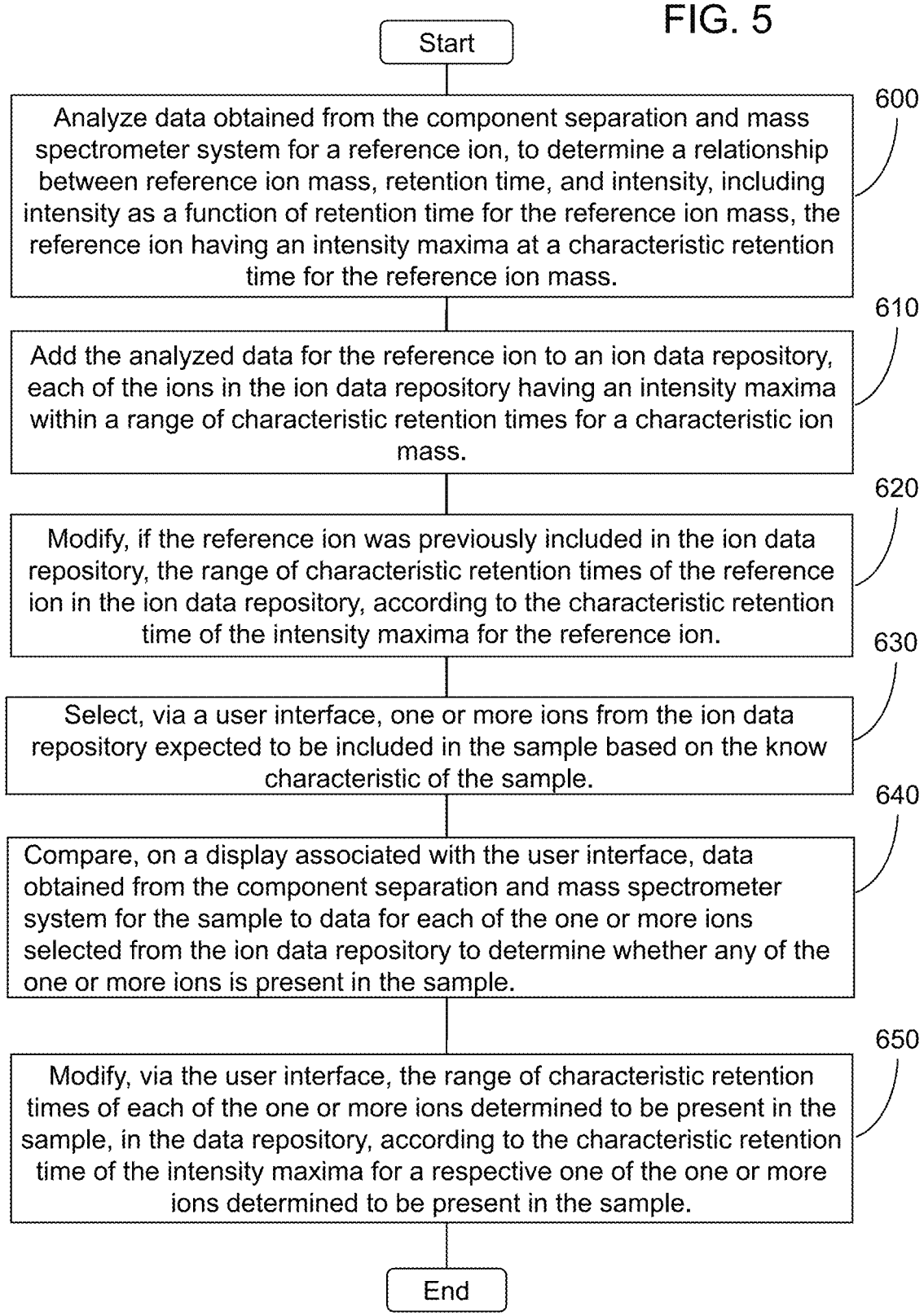
Figure 6:
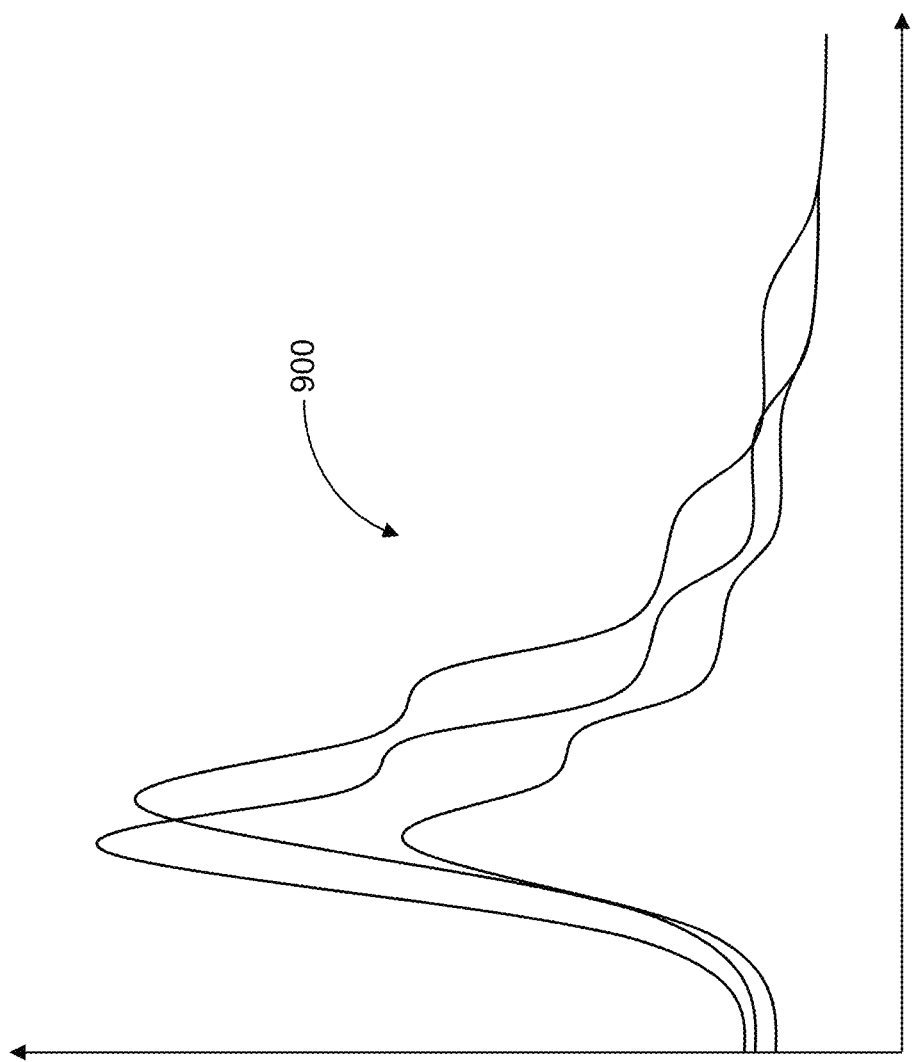
Figure 7:
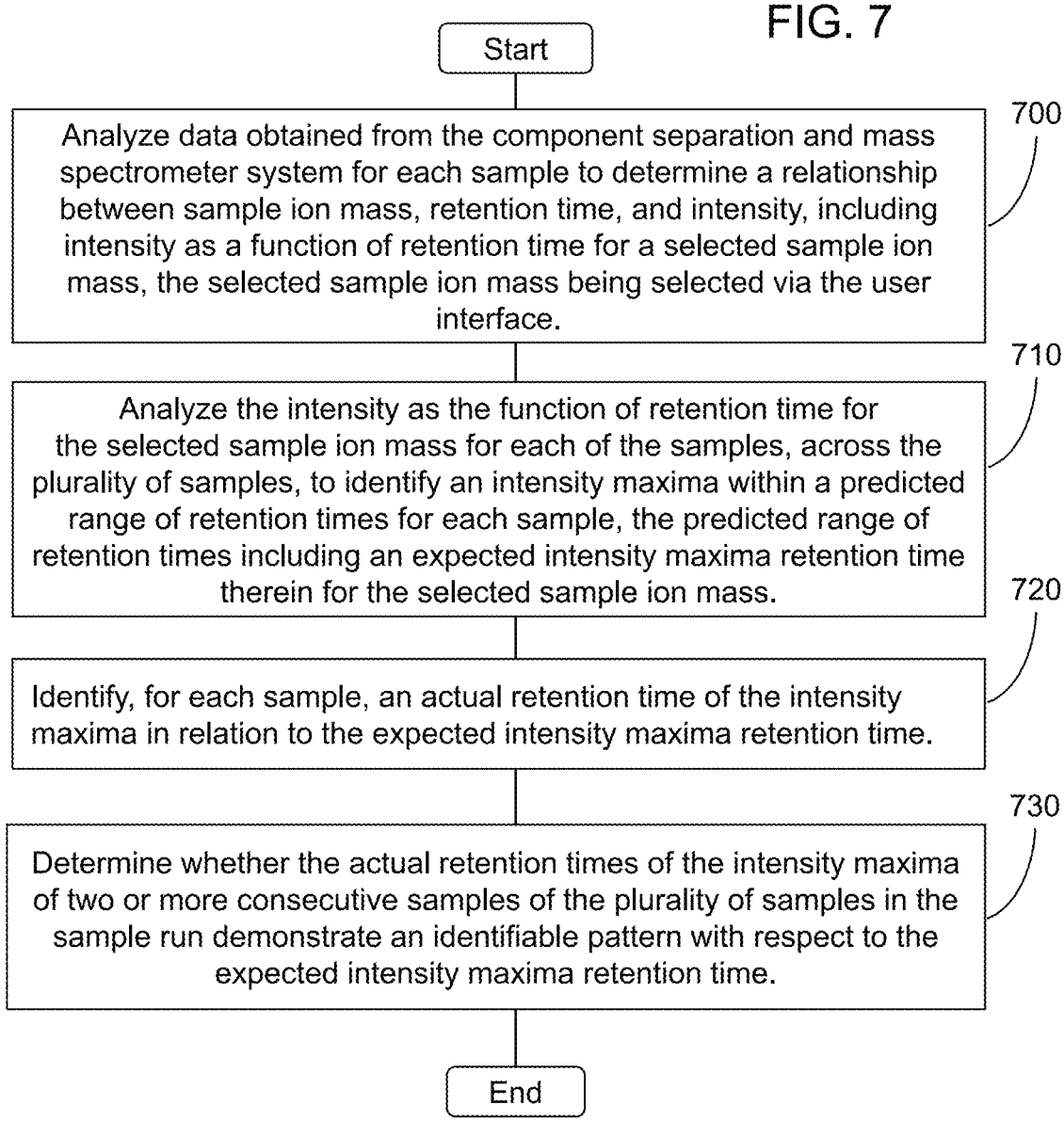
Figure 8:
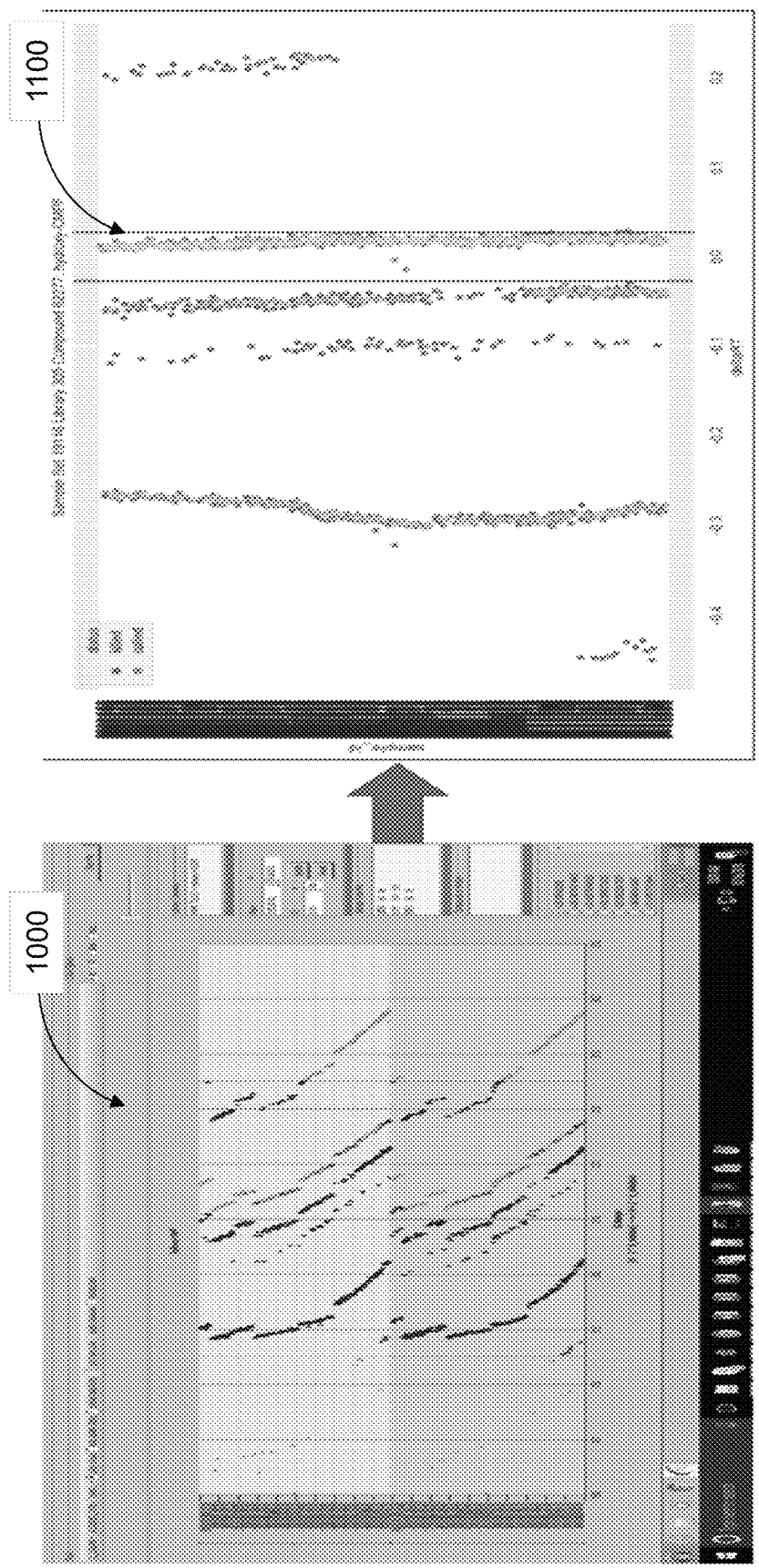

Having thus described the disclosure in general terms, reference will now be made to the accompanying drawings, which are not necessarily drawn to scale, and wherein:

FIG. 1 schematically illustrates a system according to one aspect of the present disclosure including a memory device having a database, a processor device, and a user interface (display), in communication with a spectrometry device;

FIG. 2 schematically illustrates a three-dimensional plot of spectrometry data associated with one exemplary sample;

FIG. 3 schematically illustrates a two-dimensional profile plot for one exemplary sample that may be determined from the corresponding three-dimensional plot of spectrometry data for that sample according to some aspects of the present disclosure;

FIG. 4 schematically illustrates a two-dimensional profile plot for one exemplary sample that may be determined from the corresponding three-dimensional plot of spectrometry data for that sample according to some aspects of the present disclosure;

FIG. 5 schematically illustrates an operational flow of the apparatuses, methods, and computer program products of one exemplary aspect of the present disclosure;

FIG. 6 schematically illustrates a two dimensional plot of intensity as a function of retention time for the data associated with the sample to a two dimensional plot of intensity as a function of retention time for the data associated with each of the one or more ions selected from the ion data repository, according to one aspect of the present disclosure;

FIG. 7 schematically illustrates an operational flow of the apparatuses, methods, and computer program products of one exemplary aspect of the present disclosure directed to the identification of patterns in actual data across a plurality of samples; and FIG. 8 schematically illustrates actual, uncorrected displayed data, and aligned or re-aligned displayed data as corrected, according to one aspect of the present disclosure.

DETAILED DESCRIPTION OF THE DISCLOSURE

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure is embodied in many different forms and should not be construed as limited to the embodiments set forth herein; rather, these embodiments are provided so that this disclosure will satisfy applicable legal requirements.

The various aspects of the present disclosure mentioned above, as well as many other aspects of the disclosure, are described in further detail herein. The apparatuses and methods associated with aspects of the present disclosure are exemplarily disclosed, in some instances, in conjunction with an appropriate analytical device which may, in some instances, comprise a separator portion or separation portion (e.g., a chromatograph) and/or a detector portion (e.g., a spectrometer). One skilled in the art will appreciate, however, that such disclosure is for exemplary purposes only to illustrate the implementation of various aspects of the present disclosure. Particularly, the apparatuses and methods associated with aspects of the present disclosure can be adapted to any number of processes that are used to generate complex sets of data for each sample, over/across a plurality of samples, whether biological, chemical, or biochemical, in nature. For example, aspects of the present disclosure may be used with and applied to a variety of different analytical devices and processes including, but not limited to: analytical devices including a separator portion (or "component separator" or "component separation" portion) comprising one of a liquid chromatograph (LC) and a gas chromatograph (GC); a cooperating detector portion (or "mass spectrometer" portion) comprising one of a nuclear magnetic resonance imaging (NMR) device; a mass spectrometer (MS); and an electrochemical array (EC); and/or combinations thereof. In this regard, one skilled in the art will appreciate that the aspects of the present disclosure as disclosed herein are not limited to metabolomics analysis. For example, the aspects of the present disclosure as disclosed herein can be implemented in other applications where there is a need to characterize or analyze small molecules present within a sample or complex mixture, regardless of the origin of the sample or complex mixture. For instance, the aspects of the present disclosure as disclosed herein can also be implemented in a bioprocess optimization procedure where the goal is to grow cells to produce drugs or additives, or in a drug metabolite profiling procedure where the goal is to identify all metabolites that are the result of biotranformations of an administered xenobiotic. As will be appreciated by one skilled in the art, these exemplary applications may be very different from a metabolomics analysis, where the goal is only to examine endogenous metabolites. Some other non-limiting examples of other applications could include a quality assurance procedure for consumer product manufacturing where the goal may be to objectively ensure that desired product characteristics are met, in procedures where a large number of sample components can give rise to a particular attribute, such as taste or flavor (e.g., cheese, wine or beer), or scent/smell (e.g., fragrances). One common theme thus exhibited by the aspects of the present disclosure as disclosed herein is that the small molecules in the sample can be analyzed using the various apparatus and method aspects disclosed herein.

FIG. 1 illustrates an example of a system according to one aspect of the present disclosure wherein the system is in communication with an analytical device 110, such as a combination chromatograph (component separator/component separation)/mass spectrometer. One skilled in the art will appreciate, however, that the configurations of an analytical device 110 presented herein are for exemplary purposes only, and are not intended to be limiting with respect to the scope of suitable and appropriate analytical devices that may also be applied under the principles disclosed herein As shown, a sample (whether biological, chemical, or biochemical, in nature) 100 may be introduced into the separator portion/separation portion of the analytical device 110 and analyzed using appropriate techniques, as applied through the detector portion, that will be appreciated by those skilled in the art. For example, the components of a particular sample 100 may pass through a column associated with the separator portion/separation portion, at different rates and exhibit different spectral responses (e.g., associated with intensity as a function of retention time), as detected by the detector portion, based upon their specific characteristics. As will be appreciated by one skilled in the art, the analytical device 110 may generate a set of spectrometry data, corresponding to each sample 100 and having three or more dimensions (e.g., quantifiable samples properties) associated therewith, wherein the data included in the data set generally indicates the composition of the sample 100. In some aspects, the data set may comprise, for example, data for each sample related to retention time, sample or component (ion) mass, intensity, or even sample indicia or identity. However, such data must first be appropriately analyzed in order to determine the sample composition.

In some instances, a three-dimensional data set for each of one or more samples may be selected or otherwise designated for further analysis, with each dimension corresponding to a quantifiable sample property. An example of such a three-dimensional set of spectrometry data is shown generally in FIG. 2, and may be plotted on a three-axis plot or graph, with the plot or graph including individual axes for a response intensity element 220, a sample component mass element 210, and a time element 230 (particularly, in this example, the retention time or the time that a particular component spends in the column of the separator portion of the analytical device 110). That is, the data obtained for a particular sample, in some aspects, includes a relationship between ion mass 210, retention time 230, and intensity 220, including intensity 220 as a function of retention time 230 for a particular ion mass 210. The location of data points in relation to the sample component mass axis 210 may be indicative, for example, of the number of individual component molecules within the sample 100 and the relative mass values for such sample components. According to other aspects of the present disclosure, other analytical devices may be used to generate a three or more dimensional set of analytical data corresponding to the sample 100. For example, the analytical device may include, but is not limited to: various combinations of a separator portion/separation portion comprising one of a liquid chromatograph (LC) (positive or negative channel) and a gas chromatograph (GC); and a cooperating detector portion comprising one of a nuclear magnetic resonance imaging (NMR) device; a mass spectrometer (MS); and an electrochemical array (EC). One skilled in the art will appreciate that such complex three or more dimensional data sets may be generated by other appropriate analytical devices that may be in communication with components of aspects of the present disclosure as described in further detail herein.

One or more samples 100 may be taken individually from a well plate 120 and/or from other types of sample containers and introduced individually into the analytical device 110 for analysis and generation of the corresponding three or more dimensional data set (see, e.g., FIG. 2). For example, individual samples 100 may be transferred from a well plate 120 to the analytical device 110 via pipette, syringe, microfluidic passageways defined by a test array, and/or other systems for transferring samples in a laboratory environment. As disclosed herein, the nature of the samples may vary considerably, generally comprising mixtures or complex mixtures including small molecules, wherein such samples may exemplarily include, but are not limited to: blood samples, urine samples, cell cultures, saliva samples, plant tissue and organs (e.g., leaves, roots, stems, flowers, etc.), plant extracts, culture media, membranes, cellular compartments/organelles, cerebral spinal fluid (CSF), milk, soda products, food products (e.g., yogurt, chocolate, juice), and/or other types of biological, chemical, and/or biochemical samples in which the metabolites and/or chemical/molecular components of interest may be present. Of these possible samples or sample types, one common aspect is that the selected sample includes a known characteristic. This known characteristic may be, for example, at least a general type or classification, a source, etc. Empirical data or other information associated with the known characteristic of the sample may be implemented to determine, for example, one or more ions, small molecules or metabolites expected to be present in such a sample having that known characteristic. That is, such information associated with the known characteristic provides a context to the sample and the data obtained therefrom via the component separation and mass spectrometer system, wherein the context provides an indicia at least as to a basic component or constituent of the sample.

As shown in FIG. 1, aspects of the present disclosure may comprise an ion data repository comprising, for example, a database (e.g., a relational database) stored at least in part, for example, as executable or accessible instructions in a memory or memory device 140 (i.e., a computer-readable storage medium having computer-readable program code portions stored therein), wherein the memory device 140 is in communication with a processor or processor device 130 (e.g., a computer device implementing a processor) for selectively executing the instructions/computer-readable program code portions in the memory device 140 to cause an apparatus to perform particular method steps and/or functions. In some instances, the memory device 140 and/or the processor device 130 may be configured to be in communication, whether directly or indirectly, with the analytical device 110 for receiving a data set (in some instances, a data set comprising three or more dimensions, wherein a data parameter such as sample indicia, sample or component (ion) mass, retention time, and intensity/response may represent any one of the dimensions of the data set), corresponding to the sample 100, therefrom. That is, the dataset received by the memory device includes, for example, data indicating a relationship between ion mass, retention time, and intensity. In some particular instances, the dataset (for each of one or more samples 100) includes data indicating intensity as a function of retention time for a particular ion mass. The processor device 130 may be in communication with the analytical device 110 via wire line (RS-232, and/or other types of wire connection) and/or wireless (such as, for example, RF, IR, or other wireless communication) techniques such that the database associated with the memory device 140/processor device 130 (and/or in communication therewith) may receive the data set from the analytical device 110 so as to be stored thereby.

Furthermore, the analytical device 110 may be in communication with one or more processor devices 130 (and associated user interfaces and/or displays 150) via a wire line and/or wireless computer network including, but not limited to: the Internet, local area networks (LAN), wide area networks (WAN), or other networking types and/or techniques that will be appreciated by one skilled in the art. The user interface/display 150 may be used to receive user input and to convey output such as, for example, displaying any or all of the communications involving the system, including the manipulations and analyses of sample data disclosed herein, as will be understood and appreciated by one skilled in the art. The database may be structured using commercially-available software, such as, for example, Oracle, Sybase, DB2, or other database software. As shown in FIG. 1, the processor device 130 may be in communication with the user interface/display 150 and the memory device 140 (such as a hard drive, memory chip, flash memory, RAM module, ROM module, and/or other memory device 140) for storing/administering the ion data repository/database, including the data sets received from the analytical device 110, whether automatically (directly) or indirectly. In addition, the memory device 140 may also be used to store other received data or information involving the sample(s) or component(s) thereof in the ion data repository/database and/or data otherwise manipulated by the processor device 130.

The processor device 130 may, in some aspects, be capable of converting each of the data sets, each including, for example, data indicating a relationship between various sample parameters such as ion mass, retention time, and intensity (see, e.g., FIG. 2, wherein the exemplary data set is a three-dimensional data set) for each of the samples, received by the memory device 140, into at least one corresponding two-dimensional data set (see, e.g., FIG. 3). The at least one two-dimensional data set may comprise, for example, a two-dimensional component "profile" of a particular sample 100 at a particular point 235 (FIG. 2) along one of the three axes of the three-dimensional data set. The particular point 235 along one of the three axes may be, for example, a particular selected sample component mass along the sample component mass axis 210. Once that particular sample component mass is selected, the resulting "slice" of the three-dimensional data set becomes the two-dimensional profile plot for the sample. That is, the resulting profile (also referred to herein as a "profile plot" as shown in FIGS. 3 and 4) illustrates that particular sample component mass detected (and the intensity of that detection) as a function of time measured from a zero point, the zero point corresponding to when the sample 100 is injected and/or otherwise introduced into the analytical device 110). For example, the processor device 130 may be configured to produce a detection intensity/response versus/as a function of sample component (retention) time two-dimensional profile of the sample for that given or selected sample component mass point 235 (see FIGS. 3 and 4, for example). The "x" axis in FIG. 2 (or (retention) time axis 230, for example) may further, in some instances, be characterized as a retention index and/or a retention time. Thus, the processor device 130 may be further capable of parsing each of the three (or more) dimensional data sets, for each of the plurality of samples, into one or more individual two-dimensional (i.e., intensity/response versus sample component retention time profile) profiles corresponding to at least one particular (selected) sample component mass point (element 235, for example) so as to convert each three (or more) dimensional data set (of FIG. 2, for example) into at least one corresponding two-dimensional data set of a selected sample component (having a profile or profile plot shown, for example, in FIGS. 3 and 4) that may further be plotted as an response intensity 220 of the corresponding sample component mass versus a sample component retention time 230, and displayed on the user interface/display 150, as desired. One skilled in the art will appreciate that any amount of two-dimensional data sets or profile plots may be formed or obtained from any three or more dimensional data sets by selecting two different sample parameters at a selected particular value of a third sample parameter, and then plotting the two different sample parameters against each other in a two-dimensional plot.

According to some aspects, the processor device 130 may be configured to selectively execute the executable instructions/computer-readable program code portions stored by the memory device 140, if necessary, in cooperation with the ion data repository/database also stored by the memory device 140, so as to accomplish, for instance, the identification, quantification, representation, curation, and/or other analysis of a selected sample component (i.e., a metabolite, molecule, or ion, or portion thereof) in each of the plurality of samples, from the two-dimensional data set representing the respective sample among the plurality of samples. In doing so, the sample component of interest from the sample to be analyzed is first determined from at least one known characteristic associated with the sample. The at least one known characteristic associated with the sample may include, for example, at least a general type or classification, a source, etc. In some aspects, the at least one known characteristic may involve a particular nature of the sample, wherein the particular nature of the sample may vary considerably, from generally comprising mixtures or complex mixtures including small molecules, to particularly and exemplarily including, without limitation: blood samples, urine samples, cell cultures, saliva samples, plant tissue and organs (e.g., leaves, roots, stems, flowers, etc.), plant extracts, culture media, membranes, cellular compartments/organelles, cerebral spinal fluid (CSF), milk, soda products, food products (e.g., yogurt, chocolate, juice), and/or other types of biological, chemical, and/or biochemical samples. The at least one known characteristic, in particular aspects, indicates which metabolites and/or chemical/molecular components of interest may be present in that sample. That is, in addition to data regarding discrete particular ions, the ion data repository/database may also include empirical data or other information associated with the known characteristic of the sample.

Accordingly, upon identifying the at least one known characteristic of the sample or receiving the at least one known characteristic as an input via the user interface/display 150, the processor 130 may be configured to execute computer-readable program code portions stored by the memory device 140 for implementing the empirical data and other information to correlate the one or more known characteristics with one or more particular ions, small molecules or metabolites expected to be present in such a sample having that known characteristic. That is, in some aspects, such information and empirical data associated with the one or more known characteristics provides a context to the sample and the data obtained therefrom, wherein the context provides an indicium at least as to a basic component or constituent of the sample, or where relevant data may be located within the ion data repository/database. In turn, the particular identifying data associated with the indicium of the basic component or constituent, or information location within the ion data repository/database, further indicates candidate ions, compounds and components that may be present or are expected or predicted to be present in the sample under analysis. That is, in particular aspects, comparing the known characteristic to empirical data included in the ion data repository, wherein the empirical data includes relational information between known characteristics and certain ions, allows the determination therefrom of the one or more ions corresponding to the known characteristic(s). In particular aspects of the disclosure, the selecting, based on the known characteristic, of one or more ions from the ion data repository expected to be included in the sample may be facilitated by more extensive information and empirical data received and housed within the ion data repository/database, wherein any "learning" by the processor 130 represents efficiencies and accuracies gained from additional correlative information.

As such, one aspect of the present disclosure involves the inclusion of data and information regarding the analysis of all samples into the ion data repository/database such that this "historical data" can be used to supplement the predictions and analyses for future analyzed samples. That is, more robust data and information included in the ion data repository/database, wherein such data and information in continually supplemented by additional sample analyses and inclusion of externally sourced information, could lead to more accurate designations of one or more ions or other components that are expected to be present in the data for a particular sample, as well as more efficient comparison of data for the particular sample to data for the one or more expected ions selected from the ion data repository/database to identify any of the one or more ions that is actually present in the sample in a verification/curation process. In particular aspects, the robust data and information in the ion repository/database does not necessarily need to be all correlative, but may also be any or all of inconsistent, contrary, or otherwise noncontributory toward a particular conclusion. That is "truths" as well as "untruths" or "non-truths" may all be necessarily included in the ion data repository/database to provide a complete and robust ion data repository/database for the purposes detailed herein.

In some aspects, to facilitate the analysis of a sample having known characteristics, it may also be helpful to have data associated with a standard or reference included in the analysis. Accordingly, in some aspects, a reference ion (though a reference ion is specified here, one skilled in the art will appreciate that such a reference ion may be interchangeable with a reference compound, reference sample component, or any other reference or standard suitable for data analysis in a similar manner as the sample), may be implemented in the component separation and mass spectrometer system in a separate run from the sample or contemporaneously with the sample, or the reference ion can otherwise be included in the sample itself in a single run through the component separation and mass spectrometer system.

According to aspects of the present disclosure, the processor 130 may be configured to execute computer-readable program code portions stored by the memory device 140 for analyzing data obtained from the component separation and mass spectrometer system for a reference ion (whether that reference ion is included in a separate run from the sample, run contemporaneously with the sample, or otherwise included in the sample and run together) to determine one or more relationships within the data, such as between reference ion mass, retention time, and intensity (see, e.g., FIG. 5, block 600). Such one or more relationships, in some aspects, particularly include intensity as a function of retention time for the reference ion mass. In such aspects, the reference ion has or exhibits an intensity maxima/maximum at a characteristic retention time for the reference ion mass. In this regard, one skilled in the art will appreciate that the one or more relationships, in other aspects, may particularly include, for example, intensity as a function of the ion mass for a selected retention time. Accordingly, further discussion herein referring to intensity as a function of retention time for a selected ion mass will be similarly applicable to intensity as a function of the ion mass for a selected retention time. The analysis of the reference ion (or reference sample) may, for example, provide a contemporaneous reference or indictor by which to assess the analysis of the sample(s) otherwise analyzed as disclosed herein.

Upon completion of the analysis, the processor device 130 may be configured to execute computer-readable program code portions stored by the memory device 140 for adding the analyzed data for the reference ion to the ion data repository/database, if data for the reference ion is not already included in the ion data repository (see, e.g., FIG. 5, block 610). In such instances, the data for each of the ions in the ion data repository, including data for the reference ion, is stored such that each ion has, for example, data exhibiting an intensity maxima/maximum within a range of characteristic retention times for a characteristic ion mass. That is, when a reference ion is run through the component separation and mass spectrometer system, a characteristic ion mass for that reference ion will be expected or predicted to exhibit a particular intensity maxima/maximum within an expected range of retention times.

If data for the reference ion was previously included in the ion data repository/database, the range of characteristic retention times of the reference ion in the ion data repository is modified according to the characteristic retention time of the determined intensity maxima for the reference ion (see, e.g., FIG. 5, block 620) from the analysis of the reference ion. That is, if data for the reference ion was previously included in the ion data repository and the determined intensity maxima is within the range of characteristic retention times, the range of characteristic retention times for the reference ion in the ion data repository/database is reduced accordingly (i.e., reduction of the range resulting from increase certainly of the expected retention time for the characteristic ion mass) based on a direct or indirect factor (e.g., running average, weighted average, statistical certainty, etc.). However, if the determined intensity maxima is outside the range of characteristic retention times, the range of characteristic retention times may be appropriately increased (i.e., if the determined intensity maxima is not significantly or materially outside the range). In other instances, the determined intensity maxima may not be used to affect the range of characteristic retention times, may otherwise be added to the empirical data/other information in the ion data repository/database in association with the reference ion, or the data including the determined intensity maxima may be used to determine whether any data deviation factors in the component separation and mass spectrometer system require further consideration. Such further consideration may include, for example, determining whether there has been any drift or shift in the component separation and mass spectrometer system (e.g., due to column aging), or determining whether the component separation and mass spectrometer system is being consistent between sequential runs or runs with similar samples. As previously indicated, these steps/actions are likewise similarly applicable if the particular data relationship of interest includes intensity as a function of the ion mass for a selected retention time. In such instances, the affected parameter in the ion data repository/database will be the range of characteristic ion masses for the reference ion or the particular selected ion/ion of interest.

In some aspects, the processor device 130 may be configured to execute computer-readable program code portions stored by the memory device 140 for subsequently analyzing the data obtained from the component separation and mass spectrometer system for the sample having the known characteristic to determine one or more relationships within the data such as, for example, a relationship between sample ion mass, retention time, and intensity, wherein such a relationship may particularly include intensity as a function of retention time for a selected sample ion mass. An ion present in the data for the sample may then be selected (for example, by a user from the display of the relationship of intensity as a function of retention time for the selected sample ion mass on the user interface/display 150), wherein the selected ion has an intensity maxima/maximum (e.g., an ion peak) at a characteristic retention time for the selected sample ion mass.

That is, in some aspects, the processor device 130 may be configured to execute computer-readable program code portions stored by the memory device 140 for selecting an intensity peak/maxima/maximum (see, e.g., element 225 in FIG. 4) or intensity peak/maxima/maximum arrangement (see, e.g., element 225 in FIG. 3) generally present with sufficient quality in the two-dimensional data set of metabolomics data for the sample (i.e., "at least one identifying peak"). As previously disclosed, such two-dimensional data sets are determined from respective three or more dimensional data sets of metabolomics data for the sample, generally by selecting or otherwise designating two desired dimensions/axes with each dimension/axis corresponding to a different sample parameter, and selecting a particular value (e.g., retention time or sample ion mass) with respect to another one of the dimensions/axes of the three or more dimensional data set in relation to the two different sample parameters forming the two dimensions/axes. One skilled in the art will appreciate, however, that the ion or component of the sample to be analyzed may, in some instances, be selected from the three or more dimensional data set, if necessary or desired, and that such selection of the ion or component of the sample to be analyzed may be further refined upon analysis of the two-dimensional data set corresponding thereto. In some instances, the selection of the ion or component of the sample to be analyzed may be facilitated, for example, by analyzing a graphical representation of the three or more dimensional data set(s) (i.e., via user interface or display 150, which may comprise, for example, a display device, personal computer, and/or other electronic/computer device having a display for graphical representation of data), and the selection may involve, for instance, evaluating the apparent response/intensity of that ion or component of the sample in the respective two-dimensional and/or three or more dimensional data sets, to determine the intensity peak or intensity peak arrangement 225 (i.e., "at least one identifying peak") to be user-selected for further analysis.

In this manner, the processor device 130 may also be configured, for instance, to examine intensity peak/maxima/maximum or intensity peak/maxima/maximum arrangement data that is sufficiently discernible from background noise or other undesirable data artifacts (i.e., of suitable quality), in order to reduce variances and provide a more statistically significant analysis upon determining the selected intensity peak or intensity peak arrangement 225 (i.e., "at least one identifying peak"). As referred to herein, in some instances, an "intensity peak arrangement" or combination of intensity peaks/maxima 225 may comprise, for example, a "main peak" 225A and at least one "sub-peak" 225B, 225C, 225D following on the retention time axis (see, e.g., FIG. 3). Such an "intensity peak/maxima/maximum arrangement" or combination of intensity peaks 225 may result, for example, from instances of co-elution in high throughput processing of samples through the analytical device(s). With such high throughput processing, the intensity peaks representing the various metabolites may not be detected by the analytical device(s) in such a manner as to appear "well separated" (i.e., "well resolved") from each other in the resulting data, and may thus appear as groups of intensity peaks as shown, for example, in FIG. 3. In some cases, the at least one sub-peak 225B, 225C, 225D may have a lesser intensity/response than the main peak 225A, though not necessarily always evident. In other cases, one or more of the at least one sub-peak may be evident prior to the main peak 225A on the retention time axis 230. In instances where a metabolite/ion is distinct from others in the sample (i.e., "well separated" or "well-resolved"), or in instances where the analytical device(s) receive the samples under favorable conditions, the intensity peaks representing the various metabolites may be detected by the analytical device(s) in such a manner as to appear "well-separated/well-resolved" from each other in the resulting data, and may thus appear as a separate, distinct, and/or discrete intensity peak/maxima/maximum as shown, for example, in FIG. 4.

In one aspect, in order to determine the selected intensity peak or intensity peak arrangement, the processor device 130 may be configured to first identify a plurality of candidate intensity peaks or intensity peak arrangements in the two-dimensional data set for the sample, wherein, for example, the candidate intensity peak or intensity peak arrangement with the lowest standard deviation (i.e., the best data quality of the main peak 225A across the samples) may be selected as the selected intensity/ion peak or intensity/ion arrangement 225. However, one skilled in the art will appreciate that the selected intensity peak or intensity peak arrangement may be determined in other manners. For example, upon comparing the candidate intensity peak arrangements across the two-dimensional data set for the samples, one of the candidate intensity peaks or intensity peak arrangements evident across the two-dimensional data set, and corresponding to a recognized compound, metabolite, ion, or component or portion thereof in an the associated ion data repository/database of such compounds, metabolites, ions, or components or portions thereof, may be selected via the user interface/display 150 as the selected intensity/ion peak or intensity peak arrangement. More particularly, for instance, the candidate intensity peaks or intensity peak arrangements across the two-dimensional data set may be compared with mass spectra included in the ion data repository/database housing recognized or otherwise known compounds (i.e., using a library or database matching process), followed with subjective curation or resolution of the matching process, if necessary. In such an instance, one of the candidate intensity peaks or intensity peak arrangements matched with, corresponding to, or best correlated with, the recognized or known compound (e.g., by comparison of quantitative mass) may be selected as the selected intensity/ion peak or intensity peak arrangement 225 as shown, for example, in FIGS. 3 and 4, and may facilitate or otherwise promote consistent analysis between samples.

In particular aspects, the processor device 130 may further be configured to execute instructions/computer readable program code portions so as to identify a particular compound or sample component (e.g., a metabolite) associated with the selected and analyzed intensity peak or intensity peak arrangement 225). The particular compound/sample component may be "known named" and/or "known, but unnamed" chemicals/compounds. That is, for example, the identified particular compound/sample component may correspond to a metabolite having a chemical nomenclature or to a "known, but unnamed" metabolite which has been previously identified, but not yet assigned a chemical name and/or classification. One skilled in the art will appreciate that such compound identification procedures may be accomplished in many different manners with respect to the selected intensity peak/intensity peak arrangement 225 and/or the corresponding two-dimensional or three-dimensional data set. For example, some compound identification procedures are disclosed in U.S. Pat. No. 7,433,787 (System, Method, and Computer Program Product Using a Database in a Computing System to Compile and Compare Metabolomic Data Obtained From a Plurality of Samples); U.S. Pat. No. 7,561,975 (System, Method, and Computer Program Product for Analyzing Spectrometry Data to Identify and Quantify Individual Components in a Sample); and U.S. Pat. No. 7,949,475 (System and Method for Analyzing Metabolomic Data), all assigned to Metabolon, Inc., which is also the assignee of the present application. To the extent that such compound identification procedures are relevant to the disclosure herein, such compound identification procedures disclosed by U.S. Pat. Nos. 7,433,787; 7,561,975; and 7,949,475 are incorporated herein by reference, and not otherwise discussed in detail herein for the sake of brevity.

The processor device 130 may be further configured to align the selected intensity peak or intensity peak arrangement 225 evident in the two-dimensional data set for the sample in conjunction with the collection of data associated therewith from the component separation and mass spectroscopy system, prior to further analysis of the data. More particularly, various compounds (including metabolites) may move at somewhat different rates during a separation process, from one sample to another, so that it may not be entirely clear which peaks or peak arrangements (corresponding to eluted or co-eluted compounds, for example) should be considered as corresponding to a known compound within the sample. As such, the processor device 130 may be configured to execute instructions/computer readable program code portions to implement an intensity peak/peak arrangement alignment correction method for the selected intensity peak or peak arrangement in the two-dimensional data set for the sample. For example, one such method involves spiking known compounds (e.g., a reference sample or reference ion) into each sample, wherein the known compounds are characterized by known retention times (RT) in spectrometry analysis. The set of "spiked" compounds matches a fixed retention index (RI) value to the shifting RT. The "spiked" compounds thus provide an internal standard (IS) that may be used to align data from the sample between the particular study and the ion data repository/database (i.e., chemical library). One skilled in the art will appreciate, however, that many different methods may be used to perform the intensity peak/peak arrangement alignment for the selected intensity peak or peak arrangement for the sample, within the spirit and scope of the present disclosure, and that the example presented herein in this respect is not intended to be limiting in any manner.

If the selected ion is related to or otherwise associated with the known characteristic or the reference ion, the previous analysis of the known characteristic or the reference ion may then serve as a basis for the analysis of data for the sample. For example, the direction provided by the known characteristic of the sample or the location or context of the data and information for the reference ion within the ion data repository/database may be indicative of or lead to the determination of the one or more ions expected to be present in the sample. Once the particular ion from the sample data set is selected, for example, by a user via the user interface/display 150 (see, e.g., FIG. 5, block 630), the processor device 130 may be configured to execute computer-readable program code portions stored by the memory device 140 for then comparing, on a display associated with the user interface, data obtained from the component separation and mass spectrometer system for the sample to data for each of the one or more ions selected from the ion data repository to determine whether any of the one or more ions is present in the sample (see, e.g., FIG. 5, block 640). The processor device 130 may be further configured to execute computer-readable program code portions stored by the memory device 140 for modifying, via the user interface, the range of characteristic retention times of each of the one or more ions determined to be present in the sample, in the data repository, according to the characteristic retention time of the intensity maxima for a respective one of the one or more ions determined to be present in the sample (see, e.g., FIG. 5, block 650).

In some aspects, the determination of the one or more ions expected to be present in the sample may include querying the ion data repository/database via the user interface/display 150/processor 130 to select the one or more ions therefrom based upon a retention time of an intensity maxima/maximum of the selected ion (i.e., a selected ion peak) from the data for the sample in relation to the range of characteristic retention times of the intensity maxima/maximum of the one or more ions in the ion data repository/database. That is, in some aspects, the determination of the one or more ions expected to be present in the sample may be accomplished by comparing the intensity maxima/ion peak selected from the sample data to intensity maxima/ion peaks in the ion data repository/database having characteristic retention time ranges overlapping with the retention time of the intensity maxima/ion peak selected from the sample data.

In other aspects, where the sample is one of a plurality of samples in a sample run or batch, selecting the one or more ions from the ion data repository expected to be included in the sample, based on the known characteristic, comprises selecting the one or more ions from the ion data repository determined to be present in a first one of the plurality of samples for comparing to the data for a remainder of the samples in the sample run. That is, for a multi-sample run or batch introduced to the component separation and mass spectrometer system, the one or more ions determined as expected/predicted to be included in the sample may serve as a context for the one or more ions expected to be included in the data for the remainder of the samples in that run/batch. In such instances, the data obtained from the multi-sample run/batch may be useful for checking or verifying consistency or drift or shift of the component separation and mass spectrometer system over the multiple sample runs.

In still other aspects, the determination of whether any of the one or more ions from the ion data repository expected to be included in the sample are actually present in the sample may be visually facilitated in the verification/curation process, for example, via the user interface/display 150. That is, the step of comparing data for the sample to data for the one or more ions selected from the ion data repository, in some instances, comprises comparing a two dimensional plot of intensity as a function of retention time for the data associated with the sample to a two dimensional plot of intensity as a function of retention time for the data associated with each of the one or more ions selected from the ion data repository, via the user interface/display 150, so as to provide a visual indication of intensity maxima therebetween for determining whether any of the one or more ions is present in the sample (see, e.g., FIG. 6, element 900).

Once the one or more ions expected to be present in the sample are determined, and any of the one or more candidate ions are identified or verified (curated) to be present in the sample, the data associated with the selected (identified/verified) ion is included in the ion data repository/database as historic/empirical data or other information associated with the identified/verified ion. That is, in particular aspects, upon completion of data analysis for a sample, empirical data from the analysis and associated with the sample is added to the ion data repository/database in relation to the any of the one or more ions determined to be present in the sample. In other instances, for example, the range of characteristic retention times of each of the one or more ions determined to be present in the sample, in the data repository, may be modified via the user interface/display 150 according to the characteristic retention time of the intensity maxima for a respective one of the one or more ions determined to be present in the sample. Further, in some aspects, the range of characteristic retention times of the ion in the ion data repository, identified to correspond to the selected ion, may also be modified according to the characteristic retention time of the intensity maxima for the selected ion once the selected ion is identified. More particularly, if the determined intensity maxima/maximum for the identified ion is within the range of characteristic retention times, the range of characteristic retention times for the identified ion in the ion data repository/database is reduced accordingly (i.e., reduction of the range resulting from increase certainly of the expected retention time for the characteristic ion mass) based on a direct or indirect factor (e.g., running average, weighted average, statistical certainty, etc.).

In another aspect, in addition to the identification (curation/verification) of compounds, ions or other sample components, the processor 130 may be configured to execute computer-readable program code portions stored by the memory device 140 for distinguishing between those compounds/ions/sample components that are present and biologically or statistically relevant in the sample(s) and those that are an artifact (e.g., either contamination of/within the sample or a manifestation of measurement noise), or are otherwise sparse or insignificant within or across the plurality of samples or sample set (i.e., not present in sufficient quantity to inform aggregate analysis across a sample set). This capability leverages the identification (curation/verification) capability disclosed herein and the comparison of analysis results from actual samples to analysis results from control samples, which may further increase the speed of the data curation/verification process disclosed herein.

For example, in some instances, artifacts may be detected by a comparison between data for actual samples and data for a consistent, previously-characterized sample (e.g., an "anchor sample"). In some particular instances, the consistent, previously characterized sample may comprise water (e.g., a water blank). Such a comparison is premised on, for example, that a compound/ion/sample component detected in the consistent, previously-characterized sample at a level (e.g. intensity) similar to the actual sample(s), or otherwise within a specified threshold in relation thereto, that compound/ion/sample component is flagged as likely being and artifact within the sample(s) and subsequently excluded from statistical analysis of the sample data.

More particularly, in some aspects, data obtained from the component separation and mass spectrometer system for an anchor sample, wherein the anchor sample is defined as a consistent, previously-characterized sample, is analyzed to determine a component ion of the anchor sample. For that component ion, a relationship between component ion mass, retention time, and intensity, including intensity as a function of retention time for the component ion mass, is also determined. The component ion will have and demonstrate an intensity maxima/maximum at a characteristic component ion retention time for the component ion mass. On the basis of the component ion mass being substantially equal to the characteristic ion mass of one of the one or more ions determined to be in the sample, the intensity maxima/maximum for the component ion at the characteristic component ion retention time, is compared to the intensity maxima/maximum for the one of the one or more ions determined to be in the sample at the characteristic retention time. As such, if the intensity maxima/maximum for the component ion and the one of the one or more ions determined to be in the sample are substantially similar, then the one of the one or more ions determined to be in the sample is designated as an artifact ion in the sample. The artifact ion can then be flagged or otherwise indicated as being excluded from further analysis of the sample data.

A sparse compound/ion/sample component may be detected by determining the occurrence/presence of the compound/ion/sample component within sample(s) across the sample set. For example, if the compound/ion/sample component is only detected in a small percentage of the samples or under a predetermined threshold of samples within the sample set, the compound/ion/sample component is excluded from further analysis since that the compound/ion/sample component will not contribute positively to the data analysis. In other instances, for example, run-day-based or detector sensitivity trend-based factors associated with the detection of the compound/ion/sample component may cause the compound/ion/sample component to be designated for more thorough analysis, but likely for exclusion from the data analysis.

More particularly, in instances where the sample comprises a plurality of samples in a sample run, the plurality of samples in the sample run is analyzed to determine a presence of one of the one or more ions from the ion data repository determined to be present in a first one of the plurality of samples, across the plurality of samples. As such, if a threshold quantity of the samples in the plurality of samples does not include the one of the one or more ions from the ion data repository determined to be present in the first one of the plurality of samples, then the one of the one or more ions determined to be present in the first one of the plurality of samples is designated as sparse ion in the plurality of samples, and excluded from further analysis of the sample data.

Fundamental to the data curation/verification disclosed herein is that the intensity peak/maxima/maximum of the analyzed sample(s) must be matched with the correct identifying compound/ion if further data analysis according to the present disclosure is to be useful/effective. As such, the processor 130 may be configured to execute computer-readable program code portions stored by the memory device 140 for performing a real time error correction functionality in instances where moderate, systemic deviations from the expected/predicted location (e.g., within a particular range of retention times) of an intensity peak/maxima/maximum are identified and corrected to provide increased accuracy of the analysis results.

For example, if there is shift/drift/or other systemic error that is not addressed in the apparatuses, methods, and computer program products disclosed herein, such issues can be approached by: 1) widening the confidence intervals of the predictions/expectations (i.e., expand the range of expected/predicted retention times), or 2) an iterative update approach. Aspects of the present disclosure implement the second approach since any deviations within the data tend to be systemic (e.g. samples run consecutively tend to demonstrate similar retention times for a given compound/ion/ sample component). As such, it may be more effective to first identify any detected ion intensity peaks/maxima, and then iteratively update or modify the predictions/expectations of retention times for the ion peaks/maxima with the new data to conform to any unexpected shift or drift of the sample data.

More particularly, in instances where the sample comprises a plurality of samples in a sample run, the data obtained from the component separation and mass spectrometer system for each sample is analyzed to determine a relationship between sample ion mass, retention time, and intensity, including intensity as a function of retention time for a selected sample ion mass, wherein the selected sample ion mass is selected via the user interface/display 150 (see, e.g., FIG. 7, element 700). The intensity is then analyzed as the function of the retention time for the selected sample ion mass for each of the samples, across the plurality of samples, to identify an intensity maxima/maximum within a predicted range of retention times for each sample, wherein the predicted range of retention times includes an expected intensity maxima/maximum retention time therein for the selected sample ion mass (see, e.g., FIG. 7, element 710). For each sample, an actual retention time of the intensity maxima/maximum in relation to the expected intensity maxima/maximum retention time is identified (see, e.g., FIG. 7, element 720), and a determination is made as to whether the actual retention times of the intensity maxima/ maximum of two or more consecutive samples of the plurality of samples in the sample run demonstrate an identifiable pattern with respect to the expected intensity maxima/maximum retention time (see, e.g., FIG. 7, element 730).

If a pattern is identifiable in the sample data, the identifiable pattern of the actual retention times of the intensity maxima/maximum of the two or more consecutive samples, with respect to the expected intensity maxima/maximum retention time, comprises a shift wherein the actual retention times of the intensity maxima/maximum are substantially consistently offset from the expected intensity maxima/ maximum retention time, or a drift wherein the actual retention times of the intensity maxima/maximum are offset by a non-constant function from the expected intensity maxima/maximum retention time. In general, the offset of the actual retention time of the intensity maxima/maximum of each of the plurality of samples in the sample run are corrected according to the identifiable pattern.

In instances where the identifiable pattern of the actual retention times of the intensity maxima of the two or more consecutive samples, with respect to the expected intensity maxima retention time, demonstrates an offset from the expected intensity maxima retention time which differs between two subsets of two or more consecutive samples in the sample run, the offset of the actual retention times of the intensity maxima of each of the plurality of samples in the sample run may be corrected according to the identifiable pattern of one of the two subsets having a majority of the samples in the sample run.

In another aspect, the data curation/verification procedure associated with the apparatuses, methods, and computer program products disclosed herein allows the sample data obtained from the component separation and mass spectrometer system to be expediently analyzed by the processor 130 configured to execute computer-readable program code portions stored by the memory device 140 data. In instances where the data from the analysis indicates systemic issues with the component separation and mass spectrometer system or other sample processing issues, the sample(s) must be re-run with properly operable instrumentation in order to obtain valid and appropriate data. The expediency of the data curation/verification process thus allows the collected data to determine indications of issues with the component separation and mass spectrometer system or other sample processing issues as soon as the analysis data is received from the CS/MS system. As a result, any required data re-runs can be ordered promptly (after addressing any issues with the CS/MS system) and there may also be cost savings in terms of preventing labor from being expended on data which would eventually be discarded, in any instance. This process also decreases the time required for addressing systemic errors, faults or issues in the CS/MS system to be identified and corrected, thereby leading to fewer samples processed therethrough which may be required to be re-run.

More particularly, in regard to the data curation/verification process disclosed herein, if comparing data obtained from the component separation and mass spectrometer system for the sample to data for each of the one or more ions selected from the ion data repository to determine whether any of the one or more ions is present in the sample, results in none of the one or more ions being present in the sample, then an instrument error associated with the component separation and mass spectrometer system can be resolved and the sample re-run through the component separation and mass spectrometer system in order to obtain replacement data for the sample(s).

The data curation/verification process disclosed herein interfaces with a user by way of the user interface/display 150. As also previously addressed, the disclosed process displays each of the one or more ions from the ion data repository expected to be included in the sample which includes an intensity peak/maxima/maximum which falls within an expected/predicted retention time range of that compound/ion/sample component. However, a conventional singular visualization as a function of retention index or as a function of retention time may be prone to drift, shift, run-day affects, and other issues which may contribute to misalignment of data between samples, which makes manual curation more time intensive and difficult, for example, from a labor and decision-making standpoint. As shown, for example, in FIG. 8, aspects of the present disclosure provide a visualization, via the user interface/ display 150, of possible intensity peaks/maxima across all samples, including the difference between each of the one or more ions from the ion data repository expected to be included in the sample which includes an intensity peak/ maxima/maximum which falls within an expected/predicted retention time range of that compound/ion/sample component, and the actual intensity as a function of retention time plot (e.g., $\Delta RT$) for the sample(s). The correction of the actual sample(s) data according to the identifiable pattern (e.g., drift, shift, etc.) as previously discussed results in an alignment or re-alignment of the actual sample(s) data separately of defects found in the pure (as collected) data representations of the intensity peaks/maxima (see, e.g., FIG. 8, element 1000 for the actual, uncorrected displayed data and element 1100 for the aligned or re-aligned displayed data as corrected herein for drift). As a result, the visualization facilitates manual curation by allowing a user to more quickly resolve compounds/ions (e.g., from a labor and decision-making standpoint). More particularly, the processor 130 may be configured to execute computer-readable program code portions stored by the memory device 140 for displaying, on the display 150 associated with the user interface, the corrected offset of the actual retention time of the intensity maxima/maximum of each of the plurality of samples in the sample run according to the identifiable pattern to provide a visualization of the corrected actual retention time of the intensity maxima of each of the plurality of samples across the plurality of samples in the sample run.

Aspects of the present disclosure also provide methods of analyzing metabolomics data, as shown generally in the operational flow diagram of FIG. 5, and as previously discussed herein. In addition to providing appropriate apparatuses and methods, aspects of the present disclosure may also provide associated computer program products for performing the functions/operations/steps disclosed above, in the form of, for example, a non-transitory computer-readable storage medium (i.e., memory device 140) having particular computer-readable program code portions stored therein by the medium that, in response to execution by the processor device 130, cause the apparatus to at least perform the steps disclosed herein. In this regard, FIG. 5 is an operational flow diagram associated with particular methods, apparatuses and computer program products according to particular aspects of the present disclosure. It will be understood that each block or step of the operational flow diagram or combinations of blocks in the operational flow diagram can be implemented by appropriate computer program instructions executed by the processor device 130. These computer program instructions may be loaded onto a computer device or other programmable apparatus for executing the functions specified in the operational flow diagram otherwise associated with the method(s) disclosed herein. These computer program instructions may also be stored in a computer-readable memory (i.e., memory device 140), so as to be accessible by a computer device or other programmable apparatus in a particular manner, such that the executable instructions stored in the computer-readable memory may produce or facilitate the operation of an article of manufacture capable of directing or otherwise executing the instructions which implement the functions specified in the operational flow diagram otherwise associated with the method(s) disclosed herein. The computer program instructions may also be loaded onto a computer device or other programmable apparatus to cause a series of operational steps to be performed on the computer device or other programmable apparatus to produce a computer-implemented process such that the instructions executed by the computer device or other programmable apparatus provide or otherwise direct appropriate steps for implementing the functions/steps specified in the operational flow diagram otherwise associated with the method(s) disclosed herein. It will also be understood that each step of the operational flow diagram, or combinations of steps in the operational flow diagram, can be implemented by special purpose hardware-based computer systems which perform the specified functions or steps, or combinations of special purpose hardware and computer instructions (software).

Many modifications and other aspects of the disclosure set forth herein will come to mind to one skilled in the art to which this disclosure pertain having the benefit of the teachings presented in the foregoing descriptions and the associated drawings. For example, in some aspects, the improved apparatus, method, and computer program product, addressing the technical issues and limitations associated with conventional metabolomic data analysis systems as identified herein, may facilitate scalability of the data curation/verification process disclosed herein. That is, the improved apparatus, method, and computer program product disclosed herein increases the speed of the data curation/verification process, wherein refinement thereof may result in the realization of curation/verification speed by several orders of magnitude over prior art technology, for example by processing data for up to 20K samples at a time with a single station. Such a single station capacity may, in turn, be scaled to multiple stations (e.g., computational units) with similar capacity, which will allow curation/verification data sets of significant size to be expediently processed.

In another example, the methods, apparatuses and computer program products according to particular aspects of the present disclosure are premised upon certain inputs or drivers or the conditions of such inputs or drivers, including:

The component separation and mass spectrometer system: The models/software/algorithms implemented in the apparatuses, methods, and computer program products of the present disclosure may respond differently depending on the state/behavior/condition of the component separation and mass spectrometer system. The component separation and mass spectrometer system may operate in distinct modes (platforms/arms) which may vary based on the cleanliness of the instrument, various environmental statuses (e.g., temperature, humidity, etc.), age of the columns, pressure applied to the columns, etc. The apparatuses, methods, and computer program products of the present disclosure integrate data based on the observed behavior of certain standards (e.g., endogenous compounds), which then drive the process for other compounds/ions in the ion data repository.

The Ion Data Repository: In this context, the ion data repository includes, for example, data regarding a collection of compounds/ions, their known general parameters, and fundamental presence, which have been observed on each arm/platform of the component separation and mass spectrometer system. In one particular example, glucose has been observed in blood samples when running platform A, wherein this observation is included in the ion data repository among known compounds/ions. Further data about the observed state of glucose is aggregated and included in the ion data repository (e.g., ion mass value/range, retention time/range, etc.). The ion data repository (e.g., the size thereof in terms of compounds/ions included therein) affects the scope of the data curation/verification process to be performed and determines the available decisions that could be made when observing data from the component separation and mass spectrometer system.

Historical Training/Empirical Data: Broadly related to the ion data repository or correction for the state of the component separation and mass spectrometer system. Historical training/empirical data mat be used to provide better characterizations of the state of the component separation and mass spectrometer system and how compounds/ions respond to this state, or to characterize the behavior of compounds/ions more generally on the platform.

The methods, apparatuses and computer program products according to particular aspects of the present disclosure are premised upon certain outputs or products, or the conditions of such outputs or products, including:

Manual Curation/Verification: A general manual curation/verification process receives data input structured, for example, as intensity peaks/maxima resulting from the operation of an arm of the component separation and mass spectrometer system. The data analysis according to aspects of the present disclosure is based upon those intensity peaks included in the library (e.g., within the mass/retention range of any compound found within the library), but provides another layer of data where the remaining intensity peaks may be identified through a relationship with compounds/ions, or otherwise excluded from the study while providing useful metadata (e.g., notes about other possible compounds/ions comprising the actual intensity peaks), analysis (e.g., sparsity, artifact), and visualizations (e.g., predictions relative to actual data).

Statistics: In light of the intensity peak/maxima/maximum predictions, statistics can immediately be computed, which may take the form of analysis of a "best" version of a compound/ion (e.g., a minimum relative standard deviation across platforms on which the compound/ion was observed), normalizations (e.g., processing the relative amounts of compounds/ions both presently and, in principle, against historical norms), comparing results to historical expectation/prediction, computing z-scores to identify compounds/ions whose behavior has deviated from expectation, etc.

Biological Inference: Predictions/expectations combined with statistical analysis drive the biological inference. For example, identified compounds/ions to which normalizations are applied and z-scores computed are compared with known pathway maps to identify up/down regulated biological infrastructure. From these insights, many analyses, such as disease state, may be derived.

Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A method of analyzing data for a sample having a known characteristic, the data for the sample being obtained from a component separation and mass spectrometer system, said method comprising:

analyzing data obtained from the component separation and mass spectrometer system for a reference ion, to determine a relationship between reference ion mass, retention time, and intensity, including intensity as a function of retention time for the reference ion mass, the reference ion having an intensity maxima at a characteristic retention time for the reference ion mass;

adding the analyzed data for the reference ion to an ion data repository, each of the ions in the ion data repository having an intensity maxima within a range of characteristic retention times for a characteristic ion mass;

modifying, if the reference ion was previously included in the ion data repository, the range of characteristic retention times of the reference ion in the ion data repository, according to the characteristic retention time of the intensity maxima for the reference ion;

selecting, via a user interface, one or more ions from the ion data repository expected to be included in the sample based on the known characteristic of the sample;

comparing, on a display associated with the user interface, data obtained from the component separation and mass spectrometer system for the sample to data for each of the one or more ions selected from the ion data repository to determine whether any of the one or more ions is present in the sample; and modifying, via the user interface, the range of characteristic retention times of each of the one or more ions determined to be present in the sample, in the data repository, according to the characteristic retention time of the intensity maxima for a respective one of the one or more ions determined to be present in the sample.

2. The method of claim 1, comprising including the reference ion in the sample.

3. The method of claim 1, comprising:

analyzing data obtained from the component separation and mass spectrometer system for the sample to determine a relationship between sample ion mass, retention time, and intensity, including intensity as a function of retention time for a selected sample ion mass, the selected sample ion mass being selected via the user interface;

selecting, via the user interface, an ion present in the data for the sample, the selected ion having an intensity maxima at a characteristic retention time for the selected sample ion mass;

comparing the data for the selected ion to the selected one or more ions in the ion data repository expected to be included in the sample based on the known characteristic of the sample, in order to determine an identity of the selected ion; and modifying the range of characteristic retention times of the ion in the ion data repository corresponding to the selected ion, according to the characteristic retention time of the intensity maxima for the selected ion.

4. The method of claim 1, wherein selecting one or more ions from the ion data repository expected to be included in the sample based on the known characteristic of the sample comprises querying the ion data repository via the user interface to select the one or more ions therefrom based upon a retention time of an intensity maxima of a selected ion from the data for the sample in relation to the range of characteristic retention times of the intensity maxima of the one or more ions in the ion data repository.

5. The method of claim 1, wherein the sample comprises a plurality of samples in a sample run, and wherein selecting one or more ions from the ion data repository expected to be included in the sample based on the known characteristic of the sample comprises selecting the one or more ions from the ion data repository in relation to ions determined to be present in a first one of the plurality of samples, the selected one or more ions related to ions determined to be present in a first one of the plurality of samples being used for comparison to the data for a remainder of the samples in the sample run.

6. The method of claim 1, wherein comparing, on a display associated with the user interface, data obtained from the component separation and mass spectrometer system for the sample to data for each of the one or more ions selected from the ion data repository comprises comparing, on the display, a two dimensional plot of intensity as a function of retention time for the sample to a two dimensional plot of intensity as a function of retention time for each of the one or more ions selected from the ion data repository so as to provide a visual indication of intensity maxima therebetween for determining whether any of the one or more ions is present in the sample.

7. The method of claim 1, wherein modifying, if the reference ion was previously included in the ion data repository, the range of characteristic retention times of the reference ion in the ion data repository, according to the characteristic retention time of the intensity maxima for the reference ion comprises reducing the range of characteristic retention times if the characteristic retention time of the intensity maxima for the reference ion is within the range of characteristic retention times; and determining whether any data deviation factors in the component separation and mass spectrometer system require consideration if the characteristic retention time of the intensity maxima for the reference ion is outside the range of characteristic retention times.

8. The method of claim 1, wherein the relationship between reference ion mass, retention time, and intensity, includes intensity as a function of the reference ion mass for a selected retention time, wherein the adding step comprises adding the analyzed data for the reference ion to an ion data repository such that each of the ions in the ion data repository have the intensity maxima within a range of characteristic ion masses for a characteristic retention time, and wherein the modifying step comprises modifying, if the reference ion was previously included in the ion data repository, the range of characteristic ion masses of the reference ion in the ion data repository, according to the characteristic ion mass of the intensity maxima for the reference ion.

9. The method of claim 1, wherein selecting one or more ions from the ion data repository comprises comparing the known characteristic to empirical data included in the ion data repository, the empirical data including relational information between known characteristics and ions, and determining therefrom the one or more ions corresponding to the known characteristic of the sample.

10. The method of claim 1, wherein, after comparing data for the sample to data for the one or more ions from the ion data repository and determining whether any of the one or more ions is present in the sample, the method comprises adding empirical data associated with the sample to the ion data repository in relation to the any of the one or more ions determined to be present in the sample.

11. The method of claim 1, comprising analyzing data obtained from the component separation and mass spectrometer system for an anchor sample, the anchor sample being defined as a consistent, previously-characterized sample, to determine a component ion of the anchor sample and a relationship between component ion mass, retention time, and intensity, including intensity as a function of retention time for the component ion mass, the component ion having an intensity maxima at a characteristic component ion retention time for the component ion mass.

12. The method of claim 11, wherein the component ion mass is substantially equal to the characteristic ion mass of one of the one or more ions determined to be in the sample, and the method comprises comparing the intensity maxima for the component ion at the characteristic component ion retention time, to the intensity maxima for the one of the one or more ions determined to be in the sample at the characteristic retention time, wherein if the intensity maxima for the component ion and the one of the one or more ions determined to be in the sample are substantially similar, then the one of the one or more ions determined to be in the sample is designated as an artifact ion in the sample.

13. The method of claim 11, wherein the anchor sample comprises water.

14. The method of claim 1, wherein the sample comprises a plurality of samples in a sample run, wherein the method comprises analyzing the plurality of samples in the sample run to determine a presence of one of the one or more ions from the ion data repository determined to be present in a first one of the plurality of samples, across the plurality of samples, and wherein if a threshold quantity of the samples in the plurality of samples does not include the one of the one or more ions from the ion data repository determined to be present in the first one of the plurality of samples, then the one of the one or more ions determined to be present in the first one of the plurality of samples is designated as sparse ion in the plurality of samples.

15. The method of claim 1, wherein the sample comprises a plurality of samples in a sample run, and wherein the method comprises:
    analyzing data obtained from the component separation and mass spectrometer system for each sample to determine a relationship between sample ion mass, retention time, and intensity, including intensity as a function of retention time for a selected sample ion mass, the selected sample ion mass being selected via the user interface;
    analyzing the intensity as the function of retention time for the selected sample ion mass for each of the samples, across the plurality of samples, to identify an intensity maxima within a predicted range of retention times for each sample, the predicted range of retention times including an expected intensity maxima retention time therein for the selected sample ion mass;
    identifying, for each sample, an actual retention time of the intensity maxima in relation to the expected intensity maxima retention time; and
    determining whether the actual retention times of the intensity maxima of two or more consecutive samples of the plurality of samples in the sample run demonstrate an identifiable pattern with respect to the expected intensity maxima retention time.

16. The method of claim 15, wherein the identifiable pattern of the actual retention times of the intensity maxima of the two or more consecutive samples, with respect to the expected intensity maxima retention time, comprises a shift wherein the actual retention times of the intensity maxima are substantially consistently offset from the expected intensity maxima retention time, or a drift wherein the actual retention times of the intensity maxima are offset by a non-constant function from the expected intensity maxima retention time, and wherein the method comprises correcting the offset of the actual retention time of the intensity maxima of each of the plurality of samples in the sample run according to the identifiable pattern.

17. The method of claim 16, comprising displaying, on the display associated with the user interface, the corrected offset of the actual retention time of the intensity maxima of each of the plurality of samples in the sample run according to the identifiable pattern to provide a visualization of the corrected actual retention time of the intensity maxima of each of the plurality of samples across the plurality of samples in the sample run.

18. The method of claim 15, wherein the identifiable pattern of the actual retention times of the intensity maxima of the two or more consecutive samples, with respect to the expected intensity maxima retention time, comprises an offset from the expected intensity maxima retention time, the offset differing between two subsets of two or more consecutive samples in the sample run, and wherein the method comprises correcting the offset of the actual retention times of the intensity maxima of each of the plurality of samples in the sample run according to the identifiable pattern of one of the two subsets having a majority of the samples in the sample run.

19. The method of claim 1, wherein, if comparing data obtained from the component separation and mass spectrometer system for the sample to data for each of the one or more ions selected from the ion data repository to determine whether any of the one or more ions is present in the sample results in none of the one or more ions being present in the sample, then the method comprises resolving an instrument error associated with the component separation and mass spectrometer system and re-running the sample through the component separation and mass spectrometer system to obtain replacement data for the sample.

20. An apparatus for analyzing data for a sample having a known characteristic, the data for the sample being obtained from a component separation and mass spectrometer system, the apparatus comprising a processor and a memory storing executable instructions that, in response to execution by the processor, cause the apparatus to at least perform the steps of:
analyzing data obtained from the component separation and mass spectrometer system for a reference ion, to determine a relationship between reference ion mass, retention time, and intensity, including intensity as a function of retention time for the reference ion mass, the reference ion having an intensity maxima at a characteristic retention time for the reference ion mass;
adding the analyzed data for the reference ion to an ion data repository, each of the ions in the ion data repository having an intensity maxima within a range of characteristic retention times for a characteristic ion mass;
modifying, if the reference ion was previously included in the ion data repository, the range of characteristic retention times of the reference ion in the ion data repository, according to the characteristic retention time of the intensity maxima for the reference ion;
selecting, via a user interface associated with the apparatus, one or more ions from the ion data repository expected to be included in the sample based on the known characteristic of the sample;
comparing, on a display associated with the user interface, data obtained from the component separation and mass spectrometer system for the sample to data for each of the one or more ions selected from the ion data repository to determine whether any of the one or more ions is present in the sample; and
modifying, via the user interface, the range of characteristic retention times of each of the one or more ions determined to be present in the sample, in the data repository, according to the characteristic retention time of the intensity maxima for a respective one of the one or more ions determined to be present in the sample.

21. The apparatus of claim 20, wherein the reference ion is included in the sample.

22. The apparatus of claim 21, wherein the component ion mass is substantially equal to the characteristic ion mass of one of the one or more ions determined to be in the sample, and wherein the memory stores executable instructions that, in response to execution by the processor, cause the apparatus to further perform the step of:
comparing the intensity maxima for the component ion at the characteristic component ion retention time, to the intensity maxima for the one of the one or more ions determined to be in the sample at the characteristic retention time, wherein if the intensity maxima for the component ion and the one of the one or more ions determined to be in the sample are substantially similar, then the one of the one or more ions determined to be in the sample is designated as an artifact ion in the sample.

23. The apparatus of claim 21, wherein the anchor sample comprises water.

24. The apparatus of claim 20, wherein the memory stores executable instructions that, in response to execution by the processor, cause the apparatus to further perform the steps of:
analyzing data obtained from the component separation and mass spectrometer system for the sample to determine a relationship between sample ion mass, retention time, and intensity, including intensity as a function of retention time for a selected sample ion mass, the selected sample ion mass being selected via the user interface;
selecting, via the user interface, an ion present in the data for the sample, the selected ion having an intensity maxima at a characteristic retention time for the selected sample ion mass;
comparing the data for the selected ion to the selected one or more ions in the ion data repository expected to be included in the sample based on the known characteristic of the sample, in order to determine an identity of the selected ion; and
modifying the range of characteristic retention times of the ion in the ion data repository corresponding to the selected ion, according to the characteristic retention time of the intensity maxima for the selected ion.

25. The apparatus of claim 20, wherein the memory stores executable instructions that, in response to execution by the processor, cause the apparatus to further perform the step of:
querying the ion data repository via the user interface to select the one or more ions therefrom based upon a retention time of an intensity maxima of a selected ion from the data for the sample in relation to the range of characteristic retention times of the intensity maxima of the one or more ions in the ion data repository.

26. The apparatus of claim 20, wherein the sample comprises a plurality of samples in a sample run, and wherein the memory stores executable instructions that, in response to execution by the processor, cause the apparatus to further perform the step of:
  selecting the one or more ions from the ion data repository in relation to ions determined to be present in a first one of the plurality of samples, the selected one or more ions related to ions determined to be present in a first one of the plurality of samples being used for comparison to the data for a remainder of the samples in the sample run.

27. The apparatus of claim 20, wherein the memory stores executable instructions that, in response to execution by the processor, cause the apparatus to further perform the step of:
  comparing, on the display, a two dimensional plot of intensity as a function of retention time for the sample to a two dimensional plot of intensity as a function of retention time for each of the one or more ions selected from the ion data repository so as to provide a visual indication of intensity maxima therebetween for determining whether any of the one or more ions is present in the sample.

28. The apparatus of claim 20, wherein the memory stores executable instructions that, in response to execution by the processor, cause the apparatus to further perform the steps of:
  reducing the range of characteristic retention times if the characteristic retention time of the intensity maxima for the reference ion is within the range of characteristic retention times; and
  determining whether any data deviation factors in the component separation and mass spectrometer system require consideration if the characteristic retention time of the intensity maxima for the reference ion is outside the range of characteristic retention times.

29. The apparatus of claim 20, wherein the relationship between reference ion mass, retention time, and intensity, includes intensity as a function of the reference ion mass for a selected retention time, and wherein the memory stores executable instructions that, in response to execution by the processor, cause the apparatus to further perform the steps of:
  adding the analyzed data for the reference ion to an ion data repository such that each of the ions in the ion data repository have the intensity maxima within a range of characteristic ion masses for a characteristic retention time; and
  modifying, if the reference ion was previously included in the ion data repository, the range of characteristic ion masses of the reference ion in the ion data repository, according to the characteristic ion mass of the intensity maxima for the reference ion.

30. The apparatus of claim 20, wherein the memory stores executable instructions that, in response to execution by the processor, cause the apparatus to further perform the steps of:
  comparing the known characteristic to empirical data included in the ion data repository, the empirical data including relational information between known characteristics and ions; and
  determining therefrom the one or more ions corresponding to the known characteristic of the sample.

31. The apparatus of claim 20, wherein the memory stores executable instructions that, in response to execution by the processor, cause the apparatus to further perform the step of:
  adding empirical data associated with the sample to the ion data repository in relation to the any of the one or more ions determined to be present in the sample, after comparing data for the sample to data for the one or more ions from the ion data repository and determining whether any of the one or more ions is present in the sample.

32. The apparatus of claim 20, wherein the memory stores executable instructions that, in response to execution by the processor, cause the apparatus to further perform the step of:
  analyzing data obtained from the component separation and mass spectrometer system for an anchor sample, the anchor sample being defined as a consistent, previously-characterized sample, to determine a component ion of the anchor sample and a relationship between component ion mass, retention time, and intensity, including intensity as a function of retention time for the component ion mass, the component ion having an intensity maxima at a characteristic component ion retention time for the component ion mass.

33. The apparatus of claim 20, wherein the sample comprises a plurality of samples in a sample run, and wherein the memory stores executable instructions that, in response to execution by the processor, cause the apparatus to further perform the step of:
  analyzing the plurality of samples in the sample run to determine a presence of one of the one or more ions from the ion data repository determined to be present in a first one of the plurality of samples, across the plurality of samples, wherein if a threshold quantity of the samples in the plurality of samples does not include the one of the one or more ions from the ion data repository determined to be present in the first one of the plurality of samples, then the one of the one or more ions determined to be present in the first one of the plurality of samples is designated as sparse ion in the plurality of samples.

34. The apparatus of claim 20, wherein the sample comprises a plurality of samples in a sample run, and wherein the memory stores executable instructions that, in response to execution by the processor, cause the apparatus to further perform the steps of:
  analyzing data obtained from the component separation and mass spectrometer system for each sample to determine a relationship between sample ion mass, retention time, and intensity, including intensity as a function of retention time for a selected sample ion mass, the selected sample ion mass being selected via the user interface;
  analyzing the intensity as the function of retention time for the selected sample ion mass for each of the samples, across the plurality of samples, to identify an intensity maxima within a predicted range of retention times for each sample, the predicted range of retention times including an expected intensity maxima retention time therein for the selected sample ion mass;
  identifying, for each sample, an actual retention time of the intensity maxima in relation to the expected intensity maxima retention time; and
  determining whether the actual retention times of the intensity maxima of two or more consecutive samples of the plurality of samples in the sample run demonstrate an identifiable pattern with respect to the expected intensity maxima retention time.

35. The apparatus of claim 34, wherein the identifiable pattern of the actual retention times of the intensity maxima of the two or more consecutive samples, with respect to the expected intensity maxima retention time, comprises a shift wherein the actual retention times of the intensity maxima are substantially consistently offset from the expected intensity maxima retention time, or a drift wherein the actual retention times of the intensity maxima are offset by a non-constant function from the expected intensity maxima retention time, and wherein the memory stores executable instructions that, in response to execution by the processor, cause the apparatus to further perform the step of:

correcting the offset of the actual retention time of the intensity maxima of each of the plurality of samples in the sample run according to the identifiable pattern.

36. The apparatus of claim 35, wherein the memory stores executable instructions that, in response to execution by the processor, cause the apparatus to further perform the step of:

displaying, on the display associated with the user interface, the corrected offset of the actual retention time of the intensity maxima of each of the plurality of samples in the sample run according to the identifiable pattern to provide a visualization of the corrected actual retention time of the intensity maxima of each of the plurality of samples across the plurality of samples in the sample run.

37. The apparatus of claim 34, wherein the identifiable pattern of the actual retention times of the intensity maxima of the two or more consecutive samples, with respect to the expected intensity maxima retention time, comprises an offset from the expected intensity maxima retention time, the offset differing between two subsets of two or more consecutive samples in the sample run, and wherein the memory stores executable instructions that, in response to execution by the processor, cause the apparatus to further perform the step of:

correcting the offset of the actual retention times of the intensity maxima of each of the plurality of samples in the sample run according to the identifiable pattern of one of the two subsets having a majority of the samples in the sample run.

38. The apparatus of claim 20, wherein, if comparing data obtained from the component separation and mass spectrometer system for the sample to data for each of the one or more ions selected from the ion data repository to determine whether any of the one or more ions is present in the sample results in none of the one or more ions being present in the sample, the memory stores executable instructions that, in response to execution by the processor, then cause the apparatus to further perform the step of:

resolving an instrument error associated with the component separation and mass spectrometer system and re-running the sample through the component separation and mass spectrometer system to obtain replacement data for the sample.

39. A computer program product for analyzing data for a sample having a known characteristic, the data for the sample being obtained from a component separation and mass spectrometer system, the computer program product comprising at least one non-transitory computer readable storage medium having computer-readable program code stored thereon, the computer-readable program code comprising program code for performing the steps of:

analyzing data obtained from the component separation and mass spectrometer system for a reference ion, to determine a relationship between reference ion mass, retention time, and intensity, including intensity as a function of retention time for the reference ion mass, the reference ion having an intensity maxima at a characteristic retention time for the reference ion mass;

adding the analyzed data for the reference ion to an ion data repository, each of the ions in the ion data repository having an intensity maxima within a range of characteristic retention times for a characteristic ion mass;

modifying, if the reference ion was previously included in the ion data repository, the range of characteristic retention times of the reference ion in the ion data repository, according to the characteristic retention time of the intensity maxima for the reference ion;

selecting, via a user interface associated with the apparatus, one or more ions from the ion data repository expected to be included in the sample based on the known characteristic of the sample;

comparing, on a display associated with the user interface, data obtained from the component separation and mass spectrometer system for the sample to data for each of the one or more ions selected from the ion data repository to determine whether any of the one or more ions is present in the sample; and modifying, via the user interface, the range of characteristic retention times of each of the one or more ions determined to be present in the sample, in the data repository, according to the characteristic retention time of the intensity maxima for a respective one of the one or more ions determined to be present in the sample.

40. The computer program product according to claim 39, wherein the reference ion is included in the sample.

41. The computer program product according to claim 39, wherein the computer program product comprises program code for:

analyzing data obtained from the component separation and mass spectrometer system for the sample to determine a relationship between sample ion mass, retention time, and intensity, including intensity as a function of retention time for a selected sample ion mass, the selected sample ion mass being selected via the user interface;

selecting, via the user interface, an ion present in the data for the sample, the selected ion having an intensity maxima at a characteristic retention time for the selected sample ion mass;

comparing the data for the selected ion to the selected one or more ions in the ion data repository expected to be included in the sample based on the known characteristic of the sample, in order to determine an identity of the selected ion; and modifying the range of characteristic retention times of the ion in the ion data repository corresponding to the selected ion, according to the characteristic retention time of the intensity maxima for the selected ion.

42. The computer program product according to claim 39, wherein the computer program product comprises program code for:

querying the ion data repository via the user interface to select the one or more ions therefrom based upon a retention time of an intensity maxima of a selected ion from the data for the sample in relation to the range of characteristic retention times of the intensity maxima of the one or more ions in the ion data repository.

43. The computer program product according to claim 39, wherein the sample comprises a plurality of samples in a sample run, and wherein the computer program product comprises program code for:

selecting the one or more ions from the ion data repository in relation to ions determined to be present in a first one of the plurality of samples, the selected one or more ions related to ions determined to be present in a first one of the plurality of samples being used for comparison to the data for a remainder of the samples in the sample run.

44. The computer program product according to claim 39, wherein the computer program product comprises program code for:
    comparing a two dimensional plot of intensity as a function of retention time for the sample to a two dimensional plot of intensity as a function of retention time for each of the one or more ions selected from the ion data repository so as to provide a visual indication of intensity maxima therebetween for determining whether any of the one or more ions is present in the sample.

45. The computer program product according to claim 39, wherein the computer program product comprises program code for:
    comparing, on the display, a two dimensional plot of intensity as a function of retention time for the sample to a two dimensional plot of intensity as a function of retention time for each of the one or more ions selected from the ion data repository so as to provide a visual indication of intensity maxima therebetween for determining whether any of the one or more ions is present in the sample.

46. The computer program product according to claim 39, wherein the computer program product comprises program code for:
    modifying, if the reference ion was previously included in the ion data repository, the range of characteristic retention times of the reference ion in the ion data repository, according to the characteristic retention time of the intensity maxima for the reference ion comprises reducing the range of characteristic retention times if the characteristic retention time of the intensity maxima for the reference ion is within the range of characteristic retention times; and
    determining whether any data deviation factors in the component separation and mass spectrometer system require consideration if the characteristic retention time of the intensity maxima for the reference ion is outside the range of characteristic retention times.

47. The computer program product according to claim 39, wherein the relationship between reference ion mass, retention time, and intensity, includes intensity as a function of the reference ion mass for a selected retention time, and wherein the computer program product comprises program code for:
    adding the analyzed data for the reference ion to an ion data repository such that each of the ions in the ion data repository have the intensity maxima within a range of characteristic ion masses for a characteristic retention time; and
    modifying, if the reference ion was previously included in the ion data repository, the range of characteristic ion masses of the reference ion in the ion data repository, according to the characteristic ion mass of the intensity maxima for the reference ion.

48. The computer program product according to claim 39, wherein the computer program product comprises program code for:
    comparing the known characteristic to empirical data included in the ion data repository, the empirical data including relational information between known characteristics and ions; and
    determining therefrom the one or more ions corresponding to the known characteristic of the sample.

49. The computer program product according to claim 39, wherein, after comparing data for the sample to data for the one or more ions from the ion data repository and determining whether any of the one or more ions is present in the sample, the computer program product comprises program code for:
    adding empirical data associated with the sample to the ion data repository in relation to the any of the one or more ions determined to be present in the sample.

50. The computer program product according to claim 39, wherein the computer program product comprises program code for:
    analyzing data obtained from the component separation and mass spectrometer system for an anchor sample, the anchor sample being defined as a consistent, previously-characterized sample, to determine a component ion of the anchor sample and a relationship between component ion mass, retention time, and intensity, including intensity as a function of retention time for the component ion mass, the component ion having an intensity maxima at a characteristic component ion retention time for the component ion mass.

51. The computer program product according to claim 50, wherein the component ion mass is substantially equal to the characteristic ion mass of one of the one or more ions determined to be in the sample, and wherein the computer program product comprises program code for:
    comparing the intensity maxima for the component ion at the characteristic component ion retention time, to the intensity maxima for the one of the one or more ions determined to be in the sample at the characteristic retention time, wherein if the intensity maxima for the component ion and the one of the one or more ions determined to be in the sample are substantially similar, then the one of the one or more ions determined to be in the sample is designated as an artifact ion in the sample.

52. The computer program product according to claim 50, wherein the anchor sample comprises water.

53. The computer program product according to claim 39, wherein the sample comprises a plurality of samples in a sample run, and wherein the computer program product comprises program code for:
    analyzing the plurality of samples in the sample run to determine a presence of one of the one or more ions from the ion data repository determined to be present in a first one of the plurality of samples, across the plurality of samples, wherein if a threshold quantity of the samples in the plurality of samples does not include the one of the one or more ions from the ion data repository determined to be present in the first one of the plurality of samples, then the one of the one or more ions determined to be present in the first one of the plurality of samples is designated as sparse ion in the plurality of samples.

54. The computer program product according to claim 39, wherein the sample comprises a plurality of samples in a sample run, and wherein the computer program product comprises program code for:
    analyzing data obtained from the component separation and mass spectrometer system for each sample to determine a relationship between sample ion mass, retention time, and intensity, including intensity as a function of retention time for a selected sample ion mass, the selected sample ion mass being selected via the user interface;

analyzing the intensity as the function of retention time for the selected sample ion mass for each of the samples, across the plurality of samples, to identify an intensity maxima within a predicted range of retention times for each sample, the predicted range of retention times including an expected intensity maxima retention time therein for the selected sample ion mass;

identifying, for each sample, an actual retention time of the intensity maxima in relation to the expected intensity maxima retention time; and determining whether the actual retention times of the intensity maxima of two or more consecutive samples of the plurality of samples in the sample run demonstrate an identifiable pattern with respect to the expected intensity maxima retention time.

55. The computer program product according to claim 54, wherein the identifiable pattern of the actual retention times of the intensity maxima of the two or more consecutive samples, with respect to the expected intensity maxima retention time, comprises a shift wherein the actual retention times of the intensity maxima are substantially consistently offset from the expected intensity maxima retention time, or a drift wherein the actual retention times of the intensity maxima are offset by a non-constant function from the expected intensity maxima retention time, and wherein the computer program product comprises program code for:

correcting the offset of the actual retention time of the intensity maxima of each of the plurality of samples in the sample run according to the identifiable pattern.

56. The computer program product according to claim 55, wherein the computer program product comprises program code for:

displaying, on the display associated with the user interface, the corrected offset of the actual retention time of the intensity maxima of each of the plurality of samples in the sample run according to the identifiable pattern to provide a visualization of the corrected actual retention time of the intensity maxima of each of the plurality of samples across the plurality of samples in the sample run.

57. The computer program product according to claim 54, wherein the identifiable pattern of the actual retention times of the intensity maxima of the two or more consecutive samples, with respect to the expected intensity maxima retention time, comprises an offset from the expected intensity maxima retention time, the offset differing between two subsets of two or more consecutive samples in the sample run, and wherein the computer program product comprises program code for:

correcting the offset of the actual retention times of the intensity maxima of each of the plurality of samples in the sample run according to the identifiable pattern of one of the two subsets having a majority of the samples in the sample run.

58. The computer program product according to claim 39, wherein, if comparing data obtained from the component separation and mass spectrometer system for the sample to data for each of the one or more ions selected from the ion data repository to determine whether any of the one or more ions is present in the sample results in none of the one or more ions being present in the sample, the computer program product comprises program code for then:

resolving an instrument error associated with the component separation and mass spectrometer system and re-running the sample through the component separation and mass spectrometer system to obtain replacement data for the sample.

* * * * *